US007705333B2

(12) United States Patent
Komori et al.

(10) Patent No.: US 7,705,333 B2
(45) Date of Patent: Apr. 27, 2010

(54) EXTREME ULTRA VIOLET LIGHT SOURCE APPARATUS

(75) Inventors: Hiroshi Komori, Hiratsuka (JP); Akira Endo, Tokyo (JP)

(73) Assignees: Komatsu Ltd., Tokyo (JP); Gigaphoton Inc., Tokyo (JP)

( * ) Notice: Subject to any disclaimer, the term of this patent is extended or adjusted under 35 U.S.C. 154(b) by 181 days.

(21) Appl. No.: 11/976,276

(22) Filed: Oct. 23, 2007

(65) Prior Publication Data

US 2008/0083887 A1 Apr. 10, 2008

(51) Int. Cl.
*A61N 5/06* (2006.01)
*G01J 3/10* (2006.01)
*H05G 2/00* (2006.01)

(52) U.S. Cl. .............................. 250/504 R; 250/423 R; 250/493.1; 250/492.2; 250/492.3; 250/251; 250/424; 250/396 ML; 315/111.21; 315/111.81; 422/24; 156/345.48; 156/345.5; 378/119

(58) Field of Classification Search ............. 250/504 R, 250/423 R, 493.1, 492.2, 492.3, 251, 424, 250/396 ML; 315/111.21, 111.81; 422/24; 156/345.48, 345.5; 378/119
See application file for complete search history.

(56) References Cited

U.S. PATENT DOCUMENTS 6,987,279 B2 1/2006 Hoshino et al.
7,196,342 B2 * 3/2007 Ershov et al. ........... 250/504 R
7,271,401 B2 * 9/2007 Imai et al. ............... 250/504 R

FOREIGN PATENT DOCUMENTS

JP 2006-80255 3/2006

* cited by examiner

*Primary Examiner*—Jack I Berman
*Assistant Examiner*—Meenakshi S Sahu
(74) *Attorney, Agent, or Firm*—Wenderoth, Lind & Ponack, L.L.P.

(57) ABSTRACT

In an extreme ultra violet light source apparatus that exhausts debris including fast ions and neutral particles by the effect of a magnetic field, neutral particles emitted from plasma are efficiently ionized. The extreme ultra violet light source apparatus includes a plasma generating unit that generates plasma, that radiates at least extreme ultra violet light, through pulse operation; collective optics that collects the extreme ultra violet light radiated from the plasma; a microwave generating unit that radiates microwave through pulse operation into a space in which a magnetic field is formed to cause electron cyclotron resonance, and thereby ionizes neutral particles emitted from the plasma; a magnetic field forming unit that forms the magnetic field and a magnetic field for trapping at least ionized particles; and a control unit that synchronously controls at least the plasma generating unit and the microwave generating unit.

20 Claims, 17 Drawing Sheets

EXTREME ULTRA VIOLET LIGHT SOURCE APPARATUS

BACKGROUND OF THE INVENTION

1. Field of the Invention

The present invention relates to an extreme ultra violet (EUV) light source apparatus to be used as a light source in exposure equipment.

2. Description of a Related Art

In recent years, as semiconductor processes become finer, photolithography has been making rapid progress to finer fabrication. In the next generation, microfabrication of 100 nm to 70 nm, further, microfabrication of 50 nm or less will be required. Accordingly, in order to fulfill the requirement for microfabrication of 50 nm or less, for example, exposure equipment is expected to be developed by combining an EUV light source generating EUV light with a wavelength of about 13 nm and reduced projection reflective optics.

There are three kinds of light used as an EUV light source: an LPP (laser produced plasma) light source using plasma generating by applying a laser beam to a target (hereinafter, also referred to as "LPP EUV light source apparatus"), a DPP (discharge produced plasma) light source using plasma generating by discharge, and an SR (synchrotron radiation) light source using orbital radiation. Among them, the LPP light source has the advantages that extremely high intensity close to black body radiation can be obtained because plasma density can be considerably made larger, that light emission of only the necessary waveband can be performed by selecting the target material, and that an extremely large collection solid angle of 2π steradian can be ensured because it is a point light source having substantially isotropic angle distribution and there is no structure surrounding the light source such as electrodes. Therefore, the LPP light source is thought to be predominant as a light source for EUV lithography requiring power of several tens of watts.

Here, a principle of generating EUV light in the LPP system will be explained by referring to FIG. 14 of U.S. Pat. No. 6,987,279 B2. From a target nozzle 101, a material (target material) that is excited and turned into plasma when a laser beam is applied thereto is supplied. The target material is supplied in the form of continuous flow of a liquid or gas (target get), in the form of generated droplets (droplet target), or in the form of granular solid. To the target material, a laser beam emitted from a laser unit (drive laser) 102 and collected by a focusing lens 103 is applied. Thereby, the target material is excited and plasma 104 is generated, and various wavelength components including EUV light are radiated from the plasma. On the other hand, for example, a film in which molybdenum and silicon are alternately stacked (Mo/Si multilayer film) is formed on the reflecting surface of an EUV collector mirror 105 in order to selectively reflect a predetermined wavelength component (e.g., near 13.5 nm). By the EUV collector mirror 105, the predetermined wavelength component (EUV light) radiated from the plasma 104 is reflected and collected, and outputted to an exposure unit or the like.

In the LPP EUV light source apparatus, the influence of fast ions and fast neutral particles emitted from plasma is problematic. This is because the EUV collector mirror is located near the plasma and the reflecting surface of the mirror is sputtered and damaged by those particles.

Nevertheless, the EUV collector mirror is required to have the high surface flatness of about 0.2 nm (rms), for example, in order to maintain the high reflectance, and thus, the EUV collector mirror is very expensive. Accordingly, the longer life of the EUV collector mirror is desired in view of reduction in operation costs of an EUV exposure equipment (exposure equipment using EUV light as a light source), reduction in maintenance time, and so on. The scattered materials from the plasma including fast ions and neutral particles, and the remains of the target materials are called debris.

In order to solve this problem, U.S. Pat. No. 6,987,279 B2 discloses an extreme ultra violet light source device comprising a target supply unit for supplying a material to become a target, a laser unit for generating plasma by applying a laser beam to the target, a collection optical system for collecting extreme ultra violet light radiating from the plasma and emitting the extreme ultra violet light, and magnetic field generating means for generating a magnetic field within the collection optical system when supplied with current so as to trap charged particles emitted from the plasma. That is, in U.S. Pat. No. 6,987,279 B2, the fast ions emitted from the plasma are trapped by the effect of the magnetic field, and thereby, collision with the EUV collector mirror can be prevented. Further, U.S. Pat. No. 6,987,279 B2 also discloses that the neutral particles are applied with ultraviolet light or the like to be ionized in order to trap the neutral particles having no charge in the similar way.

Further, Japanese Patent Application Publication JP-P2006-80255A discloses an extreme ultra violet light source apparatus including a chamber in which extreme ultra violet light is generated, target supply means for supplying a material to become a target into the chamber, a laser beam source for applying a laser beam to the target to generate plasma, collective optics for collecting the extreme ultra violet light radiated from the plasma, ionizing means for ionizing neutral particles included in particles emitted from the plasma into charged particles, and a magnet for forming a magnetic field within the chamber for trapping at least the neutral particles ionized by the ionizing means. Further, JP-P2006-80255A discloses that ionization of the neutral particles is performed by allowing plasma (ionization plasma) to collide with the neutral particles, and that, as a method of generating ionization plasma, electron cyclotron resonance (ECR) is caused by radiating microwave to electrons (paragraphs 0037-0040).

Typically, in the LPP EUV light source apparatus, in view of EUV conversion efficiency and so on, plasma is generated by laser oscillation in pulse operation in which the pulse width is about several nanoseconds to several tens of nanoseconds and the repetition frequency of the continuous pulse is about 1 kHz to 10 kHz. Also, in a DPP EUV light source apparatus, plasma is generated by discharge at the repetition frequency of about 1 kHz to 10 kHz. However, JP-P2006-80255A does not disclose any characteristics and generation timing of microwave to be used for causing ECR.

Here, after plasma is generated, the length of time, in which the neutral particles emitted from the plasma are scattered, is about several microseconds. Accordingly, when microwave is continuously radiated, most of the microwave energy is not used for ionization of the neutral particles by ECR, but finally emitted as thermal energy into the chamber of the EUV light source apparatus. This fact is problematic in view of effective use of energy. Further, when thermal energy is emitted into the chamber, the generation of fine target jet or droplet target is disturbed and the state of the target becomes unstable. Especially, the target liquefied by cooling a material, which is in a gas state at normal temperature, like xenon (Xe), i.e., liquefied xenon jet or liquefied xenon drop target, for example, is sensitively affected by the temperature change around. Such instability of the target causes problems of reduction in output of generated EUV light, reduction in stability of EUV pulse energy, and so on, and further, leads to reduction in exposure performance in an EUV exposure equipment and reduction in exposure processing performance.

Further, another problem caused by continuous radiation of microwave is generation of X-ray. That is, in the case where a metal material is used as the target material or a so-called mass-limited target including a droplet target is used, the residual gas pressure within the chamber becomes lower. Accordingly, the ionization of neutral particles by ECR is effectively caused only in a period as short as several microseconds in a region near the EUV plasma where particle density is relatively high. However, the electron in the ECR state then continues to absorb the microwave energy without colliding with any neutral particles. As a result, the electron obtains extremely large kinetic energy, and finally, generates radiation (X-ray) by circling motion. The X-ray generation is a serious problem because X-ray has adverse effects on human bodies and environments.

SUMMARY OF THE INVENTION

The present invention has been achieved in view of the above-mentioned problems. A purpose of the present invention is, in an extreme ultra violet light source apparatus that exhausts debris including fast ions and neutral particles by the effect of a magnetic field, to efficiently ionize neutral particles emitted from plasma.

In order to accomplish the above purpose, an extreme ultra violet light source apparatus according to one aspect of the present invention includes: plasma generating means that generates plasma, that radiates at least extreme ultra violet light, through pulse operation; collective optics that collects the extreme ultra violet light radiated from the plasma; microwave radiating means that radiates microwave through pulse operation into a space in which a magnetic field is formed to cause electron cyclotron resonance, and thereby ionizes neutral particles emitted from the plasma; magnetic field forming means that forms the magnetic field and a magnetic field for trapping at least ionized particles; and control means that synchronously controls at least the plasma generating means and the microwave radiating means.

According to the present invention, since the microwave for causing electron cyclotron resonance is radiated in pulse in synchronization with plasma generation, the utility efficiency of microwave energy in ionization of neutral particles can be improved.

DETAILED DESCRIPTION OF THE INVENTION

Figure 1:
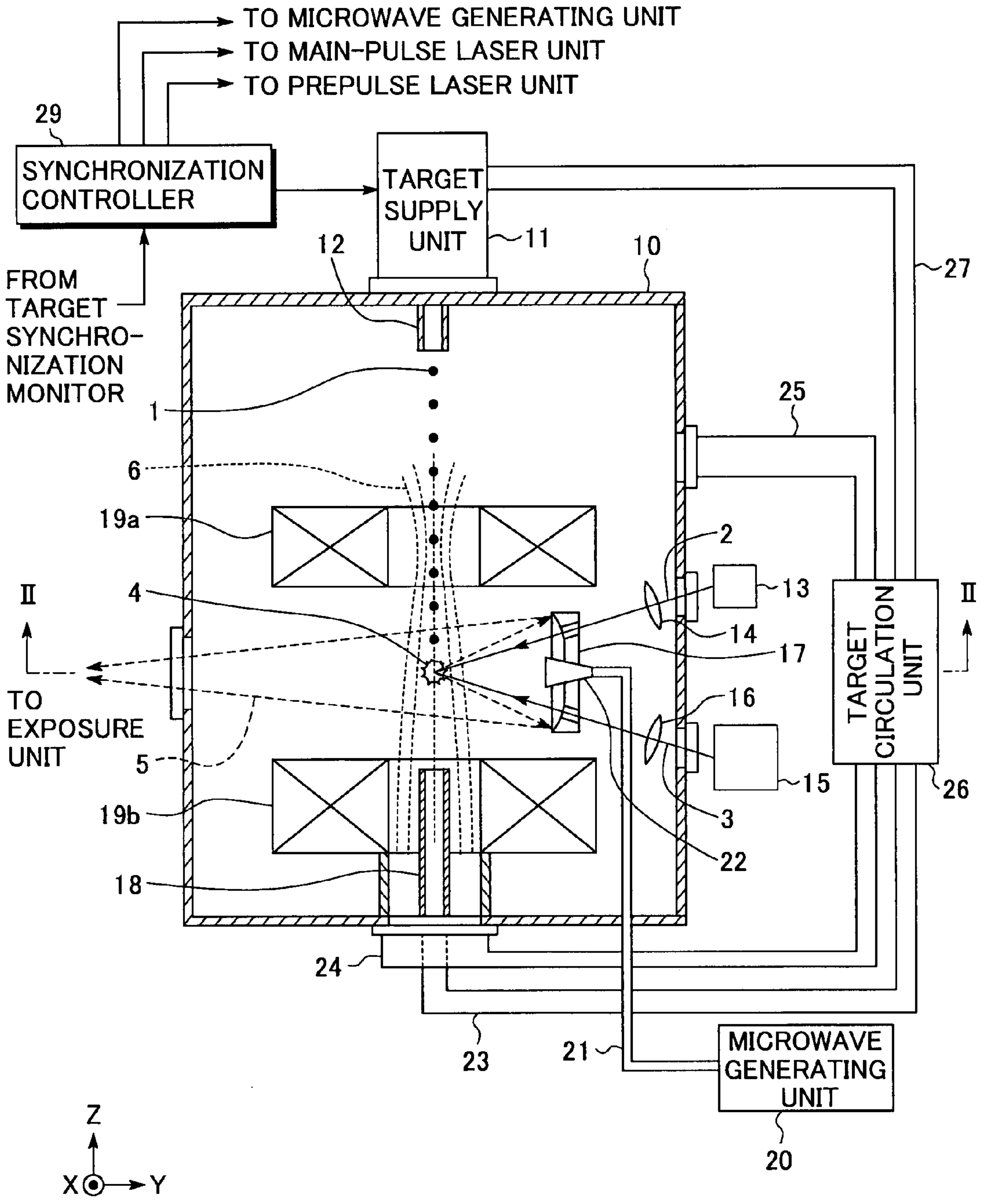
FIG. 1 shows a configuration of an extreme ultra violet light source apparatus according to the first embodiment of the present invention.

Hereinafter, preferred embodiments of the present invention will be explained in detail by referring to the drawings. The same reference numerals are assigned to the same component elements and the description thereof will be omitted.

Figure 2:
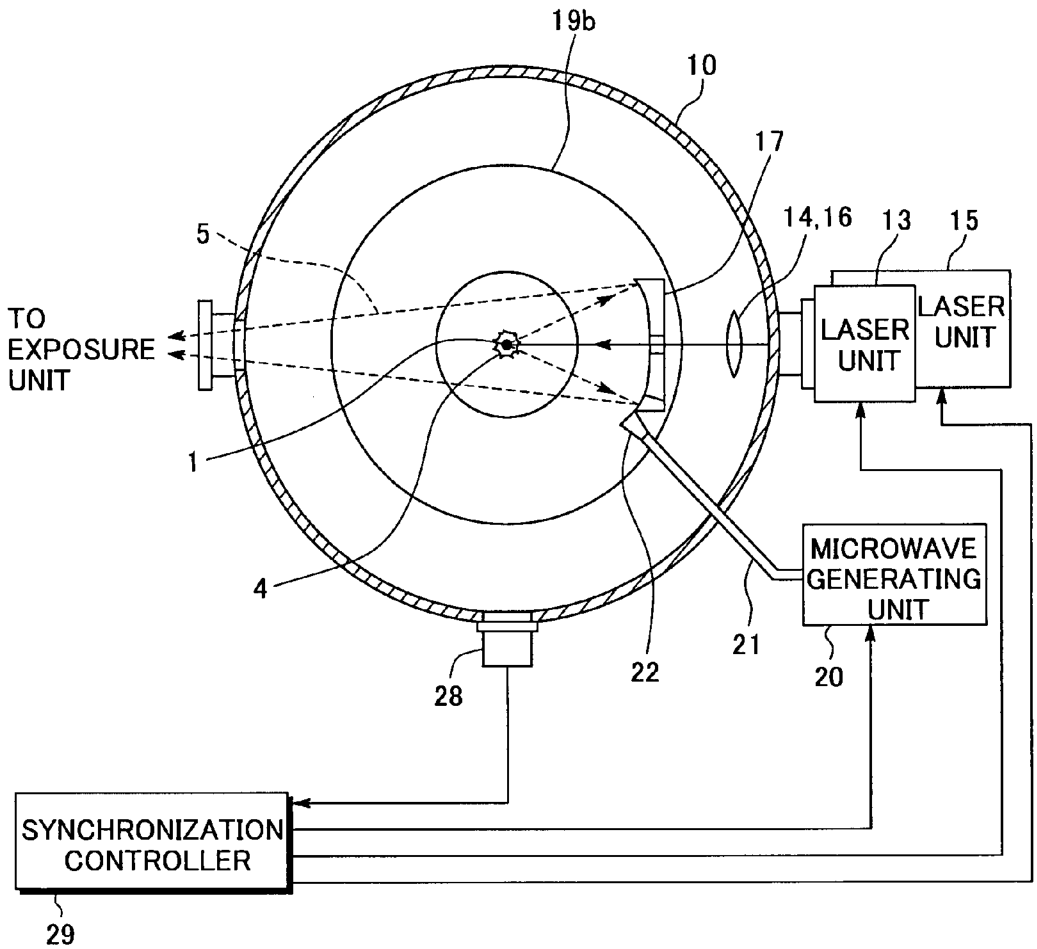
FIG. 2 shows a section along II-II shown in FIG. 1.

FIG. 1 shows a configuration of an extreme ultra violet (EUV) light source apparatus according to the first embodiment of the present invention. Further, FIG. 2 is a sectional view along II-II shown in FIG. 1. The EUV light source apparatus according to the embodiment employs a laser produced plasma (LPP) system of generating EUV light by applying a laser beam to a target material to excite the target material.

As shown in FIGS. 1 and 2, the EUV light source apparatus includes a chamber 10 in which EUV light is generated, a target supply unit 11, a target nozzle 12, a prepulse laser unit 13, a main-pulse laser unit 15, collective lenses 14 and 16, an EUV collector mirror 17, and a target collection cylinder 18. The EUV light source apparatus according to the embodiment further includes electromagnets 19*a* and 19*b*, a microwave generating unit 20, a microwave waveguide 21, a microwave antenna 22, a target collection pipe 23, an ion exhaust tube 24, a target exhaust tube 25, a target circulation unit 26, a target supply tube 27, a target synchronization monitor 28, and a synchronization controller 29.

The target supply unit 11 supplies the target nozzle 12 with a target material to be excited and thereby turned into plasma when irradiated with a laser beam. As the target material, xenon (Xe), mixture containing xenon as a primary component, argon (Ar), krypton (Kr), water ($H_2O$) or alcohol becoming gas under low-pressure condition, melted metal such as tin (Sn) and lithium (Li), water or alcohol in which fine metal particles of tin, tin oxide, copper, or the like are dispersed, ion solution formed by dissolving lithium fluoride (LiF) or lithium chloride (LiCl) in water, or the like can be used.

The state of the target material may be gas, liquid, or solid. When a target material that is in the gas state at normal temperature like xenon, for example, is used as a liquid target, the xenon gas is pressurized and cooled in the target supply unit 11 and the liquefied xenon is supplied to the target nozzle 12. On the other hand, when a material that is in the solid state at normal temperature like tin, for example, is used as a liquid target, tin is heated in the target supply unit 11 and the liquefied tin is supplied to the target nozzle 12.

The target nozzle 12 injects the target material supplied from the target supply unit 11 to feed the target material into the vacuum chamber 10. Further, the target nozzle 12 is provided with a vibration mechanism employing piezoelectric element or the like, and generates droplet target 1. Here, according to Rayleigh's stability theory of microdisturbance, when a target jet having diameter "d" and flowing at velocity "v" is vibrated at a frequency "f" to be disturbed, in the case where a wavelength "λ" (λ=v/f) of the vibration generated in the target jet satisfies a predetermined condition (e.g., λ/d=4.51), uniformly-sized droplets are repeatedly formed at the frequency "f". The frequency "f" is called Rayleigh frequency.

Both the prepulse laser unit 13 and the main-pulse laser unit 15 are laser beam sources capable of pulse oscillation at a high repetition frequency (e.g., the pulse width is about several nanoseconds to several tens of nanoseconds, and the frequency is about 1 kHz to 10 kHz). Further, the collective lenses 14 and 16 collect laser beams 2 and 3 outputted from the laser units 13 and 15, respectively, and apply them to the target material 1 injected from the target nozzle 12 in a predetermined position. In place of the collective lenses 14 and 16, collective optics employing other collective optical components or plural optical components in combination may be used.

The main-pulse laser unit 15 emits a laser beam (main pulse) 3 to be applied to the target material 1 so as to turn the target material 1 into plasma. Further, the prepulse laser unit 13 outputs a laser beam (prepulse) 2 to be previously applied to the target material 1 such that the density of the target material 1 becomes in the appropriate state when the target material 1 is applied with the main pulse 3.

Here, the target material 1 is injected from the target nozzle 12 at high-pressure (e.g., about 15 MPa) into the chamber 10 at low pressure (e.g., about 0.1 Pa), and thus, though the target material 1 is liquid at the moment of injection, the temperature thereof drastically drops due to adiabatic expansion, and then, the target material 1 is solidified. However, sometimes the density of the solidified target material may be too high for plasma generation. In such a case, the density of the target material 1 has been reduced by the previous application of the prepulse 2, and thereby, EUV light may be more efficiently generated at the time of application of the main pulse 3. The intensity of the prepulse 2 and the period from application of the prepulse 2 to application of the main pulse 3 are determined such that the target density is appropriate at the time of application of the main pulse 3 in a range where the target material 1 is not turned into plasma.

When the main pulse 3 is applied to the target material 1, plasma 4 is generated and various wavelength components are radiated from the plasma 4.

The EUV collector mirror 17 is collective optics that collects a predetermined wavelength component (e.g., EUV light near 13.5 nm) of the various wavelength components radiated from the plasma 4. The EUV collector mirror 17 has a concave reflecting surface, and a molybdenum (Mo)/silicon (Si) multilayer film for selectively reflecting the EUV light near 13.5 nm, for example, is formed on the reflecting surface. EUV light is reflected and collected in a predetermined direction (in inverted Y direction in FIG. 1) by the EUV collector mirror 17, and then, outputted to the exposure unit, for example. The collective optics of EUV light is not limited to the EUV collector mirror shown in FIG. 1, and the collective optics may be configured by employing plural optical components. However, it is necessary that the collective optics is reflection optics for suppressing absorption of EUV light.

The target collection cylinder 18 is located in a position facing the target nozzle 12 with the plasma emission point (the position where the main beam 3 is applied to the target material 1) in between. The target collection cylinder 18 collects the target material that has been injected from the target nozzle 12 but not has been applied with the laser beam and not has been turned to plasma. Thereby, the contamination of EUV collector mirror 17 and so on due to scattered unwanted target materials is prevented and reduction in degree of vacuum is prevented.

The electromagnets 19*a* and 19*b* form a magnetic field within the chamber 10 for causing electron cyclotron resonance, which will be described later, and for exhausting charged particles by the effect of the magnetic field. The coils of the electromagnets 19*a* and 19*b* are oppositely provided in parallel or substantially parallel with each other such that the centers of openings of the coils are aligned. Further, power supply units for supplying currents to the coils are connected to the electromagnets 19*a* and 19*b* through wirings. Here, since the electromagnets 19*a* and 19*b* are used within the high vacuum chamber 10, the coil windings and the cooling mechanism thereof are accommodated within an airtight container formed of non-magnetic metal such as stainless steel or ceramics or the like. Thereby, the parts such as the coil windings and so on are isolated from the vacuum space within the chamber 10, and thus, emission of contaminants is prevented and the degree of vacuum within the chamber 10 is maintained.

Each of the electromagnets 19*a* and 19*b* generates magnetic fields equal in intensity and direction to each other so as to form a mirror magnetic field in which the magnetic flux density is higher near each coil and the magnetic flux density is lower in the middle between the coils. In such a magnetic field, a charged particle (e.g., a fast ion emitted from the plasma 4 or an ionized neutral particle) is subject to Lorentz force and moves within a plane perpendicular to lines of magnetic flux while traveling in an orbiting track, and trapped near the Z-axis. Further, when the charged particle has a velocity component in the Z-direction, the particle moves while traveling in a spiral track along the Z-direction, and is exhausted to the outside of the electromagnets 19*a* and 19*b*. Thereby, the charged particle is prevented from flying near the EUV collector mirror 17 and contaminating or damaging the mirror.

Further, the intensity of the magnetic fields generated by the electromagnets 19*a* and 19*b* is changed relative to each other, and thereby, as shown by the lines of magnetic flux 6 in FIG. 1, a magnetic field vertically asymmetric with respect to the plane perpendicular to the central axis of the lines of magnetic flux. FIG. 1 shows the case where the magnetic field at the electromagnet 19*a* side is stronger than the magnetic field at the electromagnet 19*b* side. In order to change the intensity of the magnetic fields respectively generated by the electromagnets 19*a* and 19*b* relative to each other, the intensity of currents supplied to the electromagnets 19*a* and 19*b* may be changed or the number of turns and the diameters of the coils of the electromagnets 19*a* and 19*b* may be changed. There is a strong tendency of the charged particle trapped by asymmetric magnetic field to be guided toward the lower magnetic flux density (inverted Z direction in FIG. 1). Accordingly, the charged particle can be positively guided in the direction of the target collection cylinder 18 and the ion exhaust tube 24 without staying near the plasma emission point.

For more information on the mirror magnetic field and the exhaust action of charged particles by the magnetic field, refer to U.S. Pat. No. 6,987,279 B2, JP-P2006-80255A and Dwight R. Nicholson, "Introduction to Plasma Theory" (John Wiley & Sons, Inc.), chapter 2, section 6.

In the embodiment, the electromagnets are used for forming the magnetic field, however, superconducting magnets or permanent magnets may be used instead.

Figure 3A:
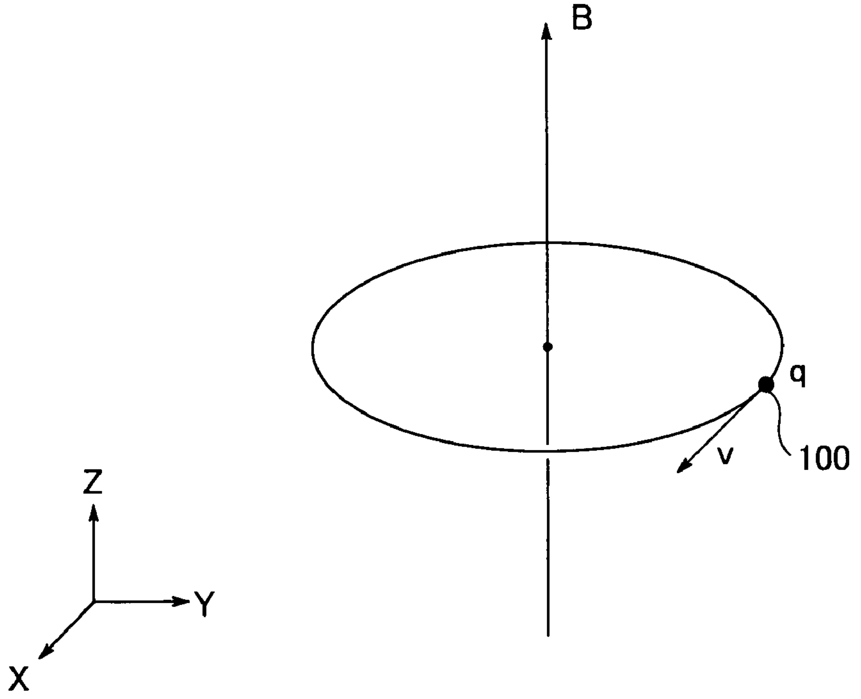
FIGS. 3A and 3B are diagrams for explanation of a principle of electron cyclotron resonance (ECR)

The microwave generating unit 20 to the microwave antenna 22 cause electron cyclotron resonance (ECR) by radiating microwave into a space in which a magnetic field is formed, and thereby ionize neutral particles (neutral debris) emitted from the plasma 4. Here, referring to FIGS. 3A and 3B, an ionization principle of neutral particles by ECR will be explained.

A moving charged particle 100 is subject to Lorentz force "F" expressed by the equation (1) in a direction constantly perpendicular to the direction of motion by a magnetic field. In the equation (1), "q" (C) is the charge of the charged particle 100, "v" (m/s) is the velocity of the charged particle 100, and "B" (T) is the magnetic flux density of the magnetic field.

$$F=q(v\times B) \quad (1)$$

Since the Lorentz force "F" acts in the direction perpendicular to the direction of motion of the charged particle 100, the charged particle 100 makes circling motion to wrap the lines of magnetic force. The circling motion is called cyclotron motion. The rotational frequency (cyclotron frequency) "f" is constant regardless of the velocity of the charged particle 100, and expressed by the following equation (2). In the equation (2), "m" (kg) is the mass of the charged particle 100.

$$F=qB/(2\pi m) \quad (2)$$

Figure 3B:
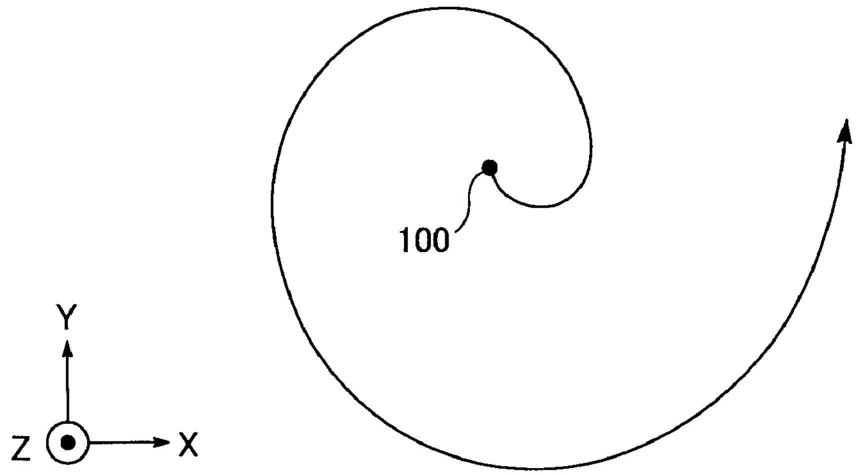

By applying an electric field (microwave) that changes at the same frequency as the frequency "f" to the charged particle 100, the charged particle 100 can efficiently obtain energy from the electric field. This is called cyclotron resonation. In the cyclotron resonation state, the charged particle 100 is constantly accelerated, and thereby, the charged particle 100 moves in a spiral track as shown in FIG. 3B.

Here, assuming that the charged particle 100 is an electron, q/2πm is about $2.8\times10^{10}$ (C/kg). Therefore, from the equation (2), the cyclotron frequency "f" (Hz) is expressed as follows.

$$F=2.8\times10^{10}B$$

For example, assuming that the magnetic flux density "B" is 0.5T, the cyclotron frequency "f" is in the microwave band of 14 GHz.

In the region where the magnetic flux density and the microwave are applied, the electron is accelerated to obtain grate kinetic energy. On the other hand, in a neutral gas (neutral particle gas) at appropriate pressure, when the kinetic energy of the electron is greater than the ionization energy of an atom that forms a neutral particle, the electron collides with the neutral particle to ionize the particle. Further, the electron, that has lost the energy for ionization of the neutral particle, obtains energy from the microwave again, and repeats collision with and ionization of the neutral particles. Accordingly, as shown in FIG. 1, by forming the magnetic field near the plasma emission point and radiating the microwave thereto, the neutral particles emitted from the plasma 4 can be ionized.

Thus ionized particles by ECR are trapped near the Z-axis by the effect of the magnetic field formed by the electromagnets 19*a* and 19*b*, and exhausted to the outside of the electromagnets 19*a* and 19*b*.

The microwave generating unit 20 shown in FIG. 1 includes a general microwave generator such as magnetron, klystron, Gunn diode, and transistor, and operates with a predetermined pulse width (several microseconds to several tens of microseconds) to generate microwave having a predetermined frequency that causes ECR.

The microwave waveguide 21 guides the microwave generated in the microwave generating unit 20 into the vacuum chamber 10. As the microwave waveguide 21, a metal waveguide, dielectric waveguide, microwave transfer cable such as a coaxial cable, and so on is used in accordance with the frequency of the microwave.

The microwave antenna 22 has an open end spreading in a horn shape, and radiates the microwave propagating via the microwave waveguide 21 into the chamber 10. The microwave antenna 22 may be provided as a member separately provided at the leading end of the microwave waveguide 21, or the leading end of the microwave waveguide 21 may be gradually spread into the horn shape to form the microwave antenna 22. A microwave amplifier may be provided at the downstream of the microwave generating unit 20 or in the middle of the microwave waveguide 21.

The target collection pipe 23 transports the target material collected by the target collection cylinder 18 to the target circulation unit 26.

The ion exhaust tube 24 has the opening connected to the central opening of the electromagnet 19*b*, and collects the charged particles emitted from the plasma 4 and guided outside of the electromagnet 19*b*, and transports them to the target circulation unit 26.

The target exhaust tube 25 is a path for exhausting the target material remaining within the chamber 10 to the outside of the chamber 10.

The target circulation unit 26 is a unit for reusing the residual target material and charged particles collected via the target collection pipe 23, the ion exhaust tube 24, and the target exhaust tube 25, and includes a suction power source (suction pump), a refining mechanism for the target material, and a pressure feed power source (pressure feed pump). The target circulation unit 26 refines the target material and so on collected from within the chamber 10 in the refining mechanism and pressure-feeds them via the target supply tube 27 to the target supply unit 11.

In order to assist the pumping action of the target circulation unit 26, exhaust pumps may be separately provided for the target collection pipe 23, the ion exhaust tube 24, and the target exhaust tube 25.

The target monitor 28 includes a CCD camera or photosensor array in which photosensors are linearly arranged and, when the target material 1 passes through a predetermined position, the target monitor 28 outputs a signal representing the time. The target monitor 28 may monitor the laser application position (i.e., the plasma emission point), or another position as long as it is correlated with the time when the target material 1 reaches the laser application position. For example, in the case where the target monitor 28 monitors a position in the track of the target material 1, the time when the target material 1 passes through the laser application position can be calculated based on the distance between the monitored position and the laser application position and the velocity of the target material 1.

The synchronization controller 29 synchronously controls the operation timing of the prepulse laser unit 13, the main-pulse laser unit 15, and the microwave generating unit 20 based on the output signal of the target monitor 28. Here, in view of the improvement in EUV conversion efficiency, the EUV light source apparatus generates EUV light by applying a laser beam (the main pulse 3) in pulse width of about several nanoseconds to several tens of nanoseconds, for example. For the purpose, the synchronization controller 29 sets synchronization and delay times of the units such that the optimization of the target density (application of the prepulse 2) and the microwave application for ionization of neutral particles by ECR may be performed with appropriate timing based on the pulse operation of the main pulse 3.

Specifically, the synchronization controller 29 sets the drive timing of the main-pulse laser unit 15 such that the target material 1 is applied with the main pulse 3 when passing through the plasma emission point. Further, the synchronization controller 29 sets the drive timing of the prepulse laser unit 13 such that the target material 1 is applied with the prepulse 2 at a predetermined time before the application of the main pulse 3.

Furthermore, the synchronization controller 29 controls the operation of the microwave generating unit 20 in the following manner. By applying the main pulse 3 to the target material 1, the plasma 4 is generated, and neutral particles are emitted from the plasma and diffused. However, the period in which appropriate particle density (appropriate gas pressure) is achieved in the application range of the microwave radiated from the microwave antenna 22 is extremely short. In order to efficiently ionize the neutral particles, electron avalanche due to ECR is necessary to occur in the period. Here, the electron avalanche is a phenomenon of chain reactions in which electrons ionize neutral particles to emit other electrons (secondary electrons) and the secondary electrons are accelerated by ECR to ionize other neutral particles, and resulting in generation of a large amount of electrons. Accordingly, the synchronization controller 29 sets the operation start timing of the microwave generating unit 20 such that the electron avalanche occurs when the gas pressure is appropriate. On the other hand, since the interior of the chamber 10 is kept in high vacuum for suppressing absorption of EUV light, the mean free path to the collision of electrons with neutral particles is relatively long. Accordingly, when the microwave continues to be radiated for a long period, the electron obtains extremely great kinetic energy by ECR, and finally, generates radiation (X-ray) by the circling motion. In order to prevent this phenomenon, the synchronization controller 29 stops the operation of the microwave generating unit 20 after a predetermined period (e.g. the period in which the appropriate gas pressure is achieved in the application range of the microwave) has elapsed from application of the main pulse 3.

Figure 4:
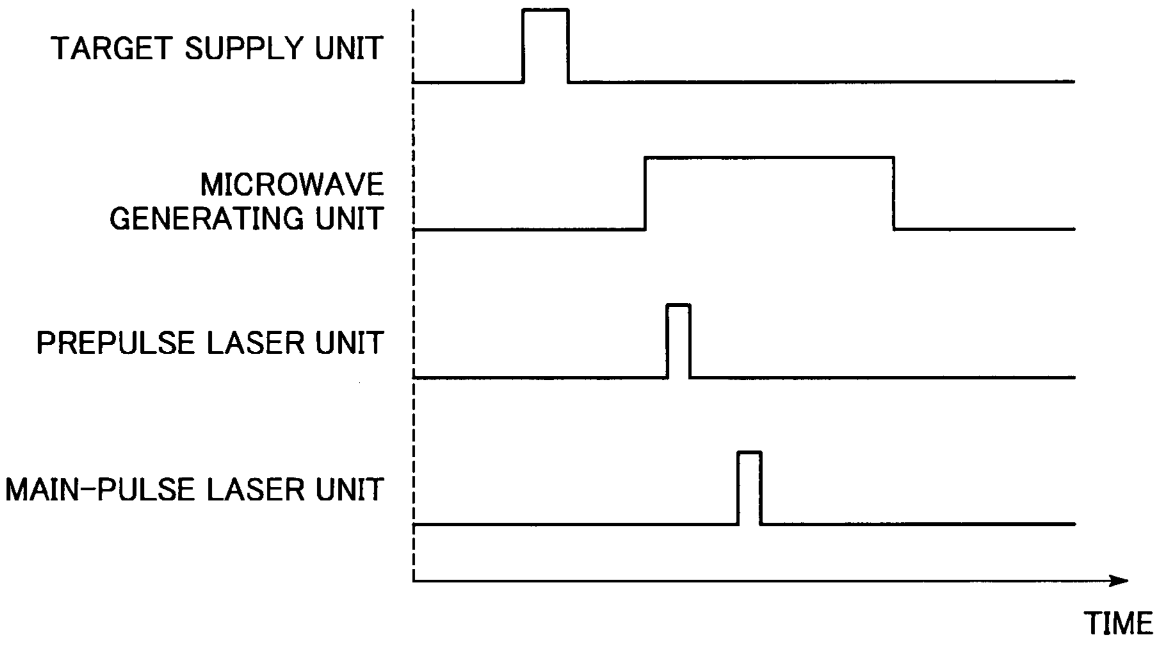
FIG. 4 is a timing chart of control signals to be outputted from a synchronization controller shown in FIG. 1.

FIG. 4 is a specific example of timing chart of control signals to be outputted from the synchronization controller 29 to the respective units. In FIG. 4, the uppermost line shows the output signal (monitor signal) of the target synchronization monitor 28, and the rising of the output signal represents the timing at which the droplet target material 1 is injected from the target nozzle 12. Further, the second line shows the control signal to be outputted to the microwave generating unit 20, and the microwave generating unit 20 radiates microwave while the control signal is at the high level. Furthermore, the third and fourth lines show the control signals for the prepulse laser unit 13 and the main-pulse laser unit 15, respectively, and the laser units 13 and 15 output laser beams while the control signals are at the high level.

In FIG. 4, the respective units are synchronously controlled such that the radiation timing of microwave is earlier than the application timing of prepulse 2 or the application timing of main pulse 3. Thereby, the time when the application range of microwave is at the appropriate gas pressure and the time when the electron avalanche occurs by ECR can be made substantially coincide with each other. As a result, the neutral particles can be efficiently ionized.

As explained above, according to the embodiment, since the pulse radiation timing of microwave and the generation timing of plasma are synchronously controlled, most of the microwave energy can be used for ionization of neutral particles (debris) emitted from EUV plasma. Especially, when the microwave radiation is started earlier than the prepulse of main pulse application to the target material, the utility efficiency of the microwave energy can be further improved, and unwanted energy emitted into the chamber 10 can be drastically reduced. Thereby, the stability of microjet target and droplet target is improved, and thus, the EUV light output can be increased and the stability of EUV pulse energy can be improved. Further, electrons no longer absorb excessive microwave energy, and thereby, the X-ray generation due to high-speed circling motion of electrons can be avoided and the safety can be improved.

Further, thus ionized particles can be quickly exhausted to the outside of the EUV collector mirror by the effect of the magnetic field, and thereby, the contamination and damage of the EUV collector mirror can be suppressed, the reduction in reflectance of the EUV collector mirror can be prevented, and the longer life of the mirror can be obtained. In addition, the stay of debris near the plasma emission point can be suppressed. As a result, the EUV light utility efficiency is improved and the exchange frequency of EUV collector mirror becomes lower, and thereby, the reduction in operation costs of the EUV light source apparatus and the improvement in operation availability can be realized. Furthermore, the stabilization in the exposure performance, the improvement in operation availability, and the improvement in exposure processing performance can be realized in an exposure system using the EUV light source apparatus, and thus, the productivity of semiconductor devices can be improved.

Figure 5:
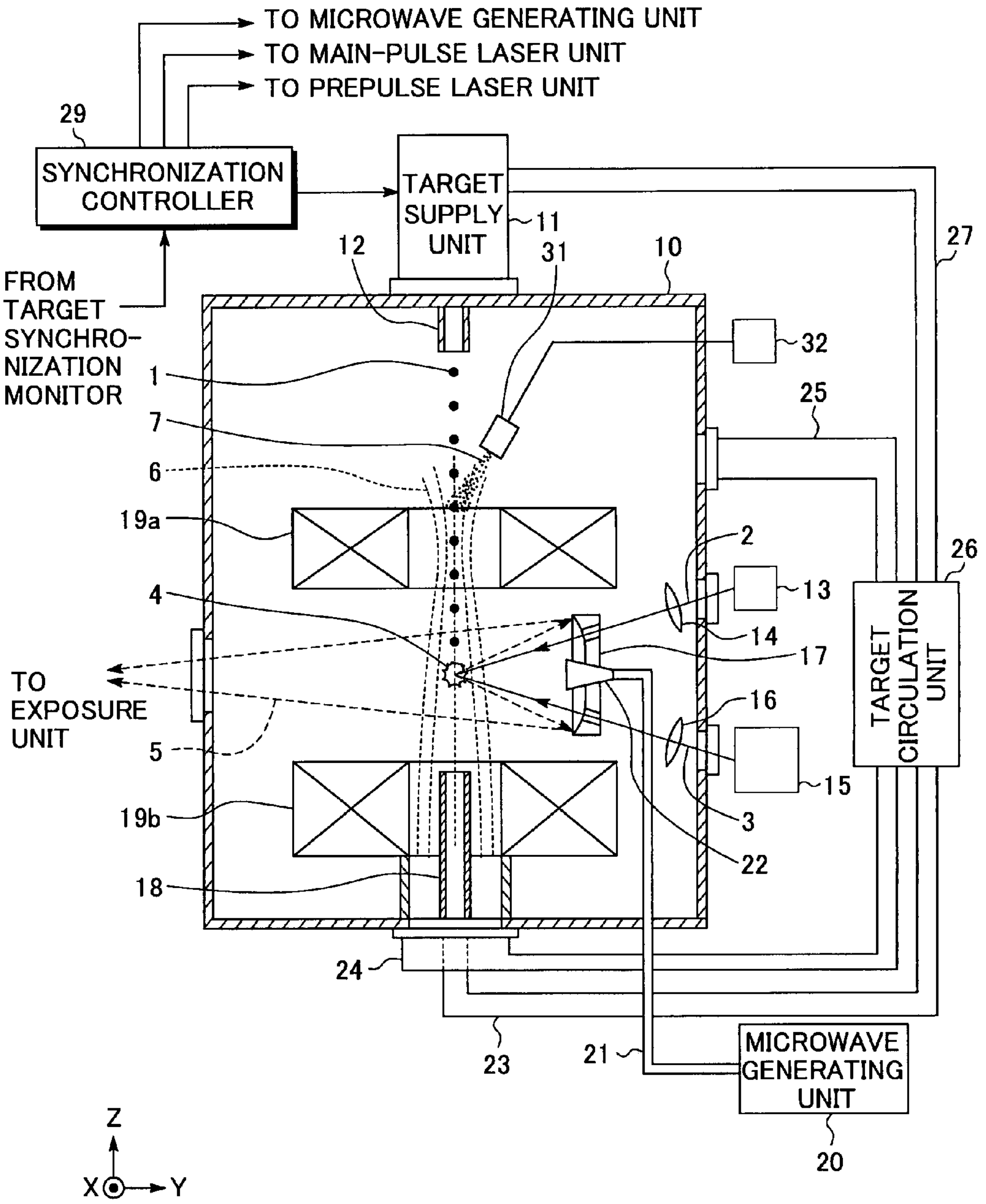
FIG. 5 shows a configuration of an extreme ultra violet light source apparatus according to the second embodiment of the present invention.

Next, an EUV light source apparatus according to the second embodiment of the present invention will be explained with reference to FIG. 5. As shown in FIG. 5, the EUV light source apparatus according to the embodiment is further provided with an electron supply unit 31 and an electron supply controller 32 in addition to the EUV light source apparatus shown in FIG. 1.

The electron supply unit 31 is a unit for supplying electrons into the chamber 10. The position where the electron supply unit 31 is provided may be anywhere in the chamber 10 as long as electrons 7 emitted from the electron supply unit 31 may be allowed to reach a region where ECR is caused (i.e., near the plasma emission point). In the embodiment, the electron supply unit 31 is provided near the central opening of the electromagnet 19*a*. The electron 7 emitted to the position is guided to the vicinity of the plasma emission point along the lines of magnetic flux 6 by the effect of the magnetic field formed by the electromagnets 19*a* and 19*b*.

The electron supply controller 32 includes a power supply unit and controls the operation of the electron supply unit 31.

Here, in the case where microwave is radiated in pulse width of several microseconds to several tens of microseconds, in order to allow the ionization of neutral particles by ECR to efficiently make progress, in the early stage of microwave radiation, the steep rising of ionization, that is, electron avalanche should be caused early. However, typically, primary electrons causing the electron avalanche randomly appear from an ionization source present in the natural environment like cosmic radiation, and thus, it is difficult to synchronize generation of the primary electrons with the pulse operation of the microwave generating unit 20. Further, there is a problem that the number of the electrons generated from the ionization source or the number of electrons existing in the background is small.

Accordingly, in the embodiment, in order to produce the electron avalanche early and reliably, the electron supply unit 31 is provided to introduce the sufficient number of primary electrons into the chamber 10. As a result, according to the embodiment, the ionization of neutral particles by ECR can be allowed to reliably and efficiently make progress.

Next, an EUV light source apparatus according to the third embodiment of the present invention will be explained with reference to FIG. 6.

Figure 6:
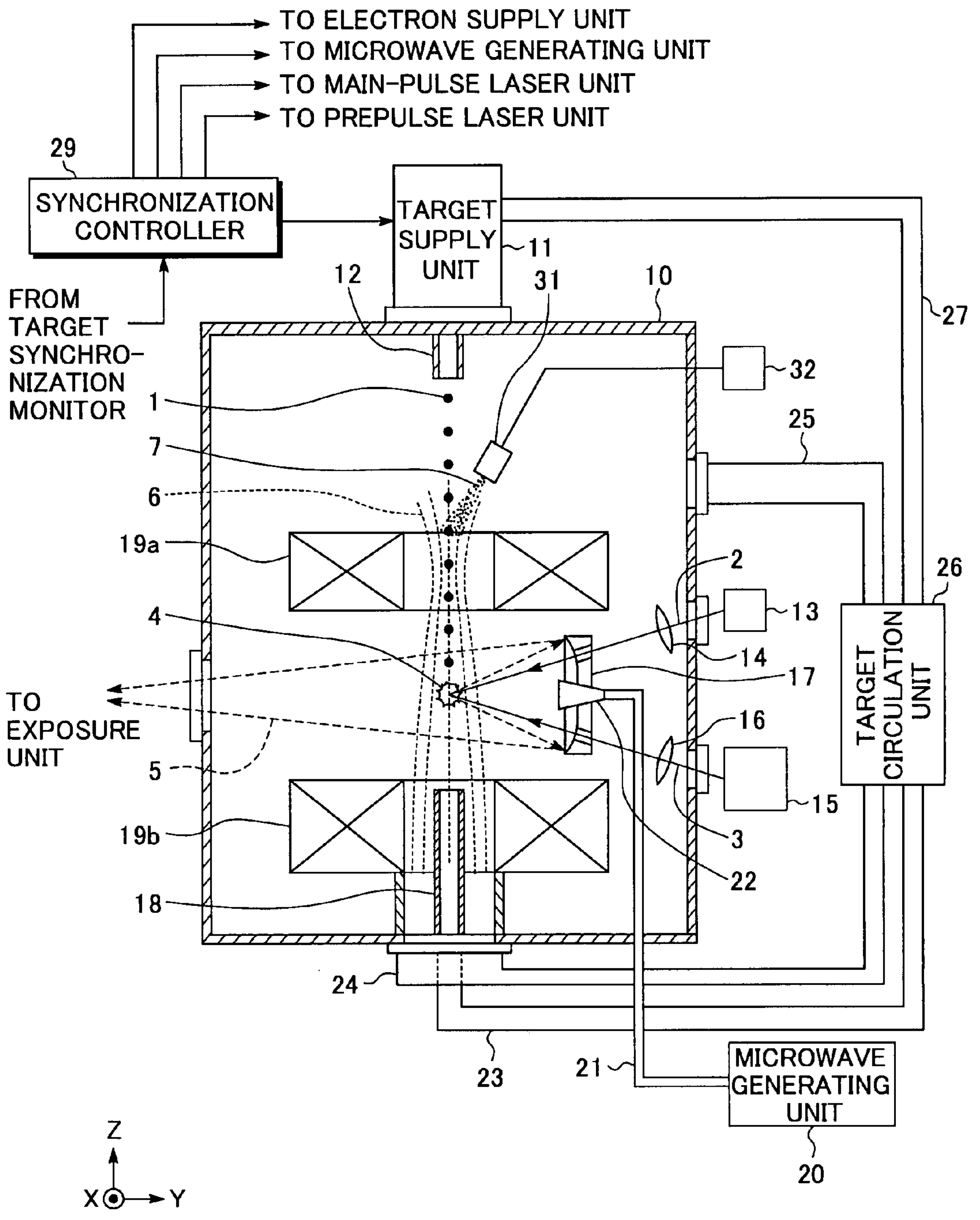
FIG. 6 shows a configuration of an extreme ultra violet light source apparatus according to the third embodiment of the present invention.

As shown in FIG. 6, the EUV light source apparatus according to the embodiment is, in the EUV light source apparatus having the electron supply unit 31 and the electron supply controller 32, to control their operation by the synchronization controller 29. The rest of the configuration is the same as that shown in FIG. 5.

In the embodiment, the operation of the electron supply controller 32 is controlled to perform pulse operation based on the radiation start timing of microwave. Thereby, the timing at which the primary electrons 7 reach the application range of the microwave and the timing at which microwave radiation is started are made coincide with each other, and thus, the electron avalanche by ECR can be reliably caused with the appropriate timing. Further, since the minimum electrons 7 are introduced into the chamber 10, the reduction in degree of vacuum of the chamber 10 and the damage on the parts within the chamber 10 due to unwanted electrons can be suppressed.

Figure 7:
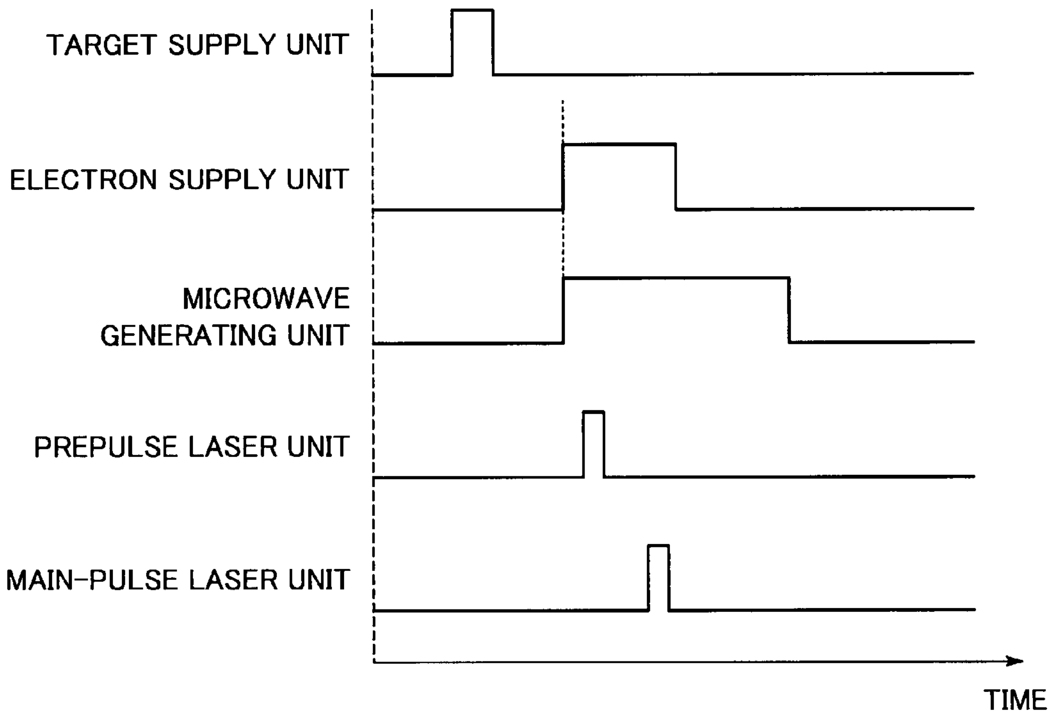
FIG. 7 is a timing chart of control signals to be outputted from a synchronization controller shown in FIG. 6.

FIG. 7 shows a specific example of timing chart of control signals to be outputted from the synchronization controller 29 to the respective units. The uppermost line shows the output signal of the target synchronization monitor 28, and the rising of the output signal represents the timing at which the droplet target material 1 is injected from the target nozzle 12. Further, the second line shows the control signal to be outputted to the electron supply controller 32, and the electron supply unit 31 emits electrons 7 while the control signal is at the high level. The third line shows the control signal to be outputted to the microwave generating unit 20, and the microwave generating unit 20 radiates microwave while the control signal is at the high level. Furthermore, the fourth and fifth lines show the control signals to be outputted to the prepulse laser unit 13 and the main-pulse laser unit 15, respectively, and the prepulse laser unit 13 and the main-pulse laser unit 15 output laser beams while the control signals are at the high level.

As shown in FIG. 7, the respective units are synchronously controlled such that the timing at which primary electrons are emitted through the pulse operation and the timing at which microwave radiation is started are made coincide with each other, and the timing is earlier than the application timing of prepulse 2 or the application timing of main pulse 3. Thereby, when the neutral particles emitted from the plasma 4 have appropriate particle density in the application range of microwave, the electron avalanche by ECR can be reliably caused. As a result, the influence of electrons on the parts within the chamber 10 can be suppressed and the neutral particles can be efficiently ionized by a large amount of electrons accelerated at a high speed. The timing at which the supply of primary electrons is ended may be earlier than the timing at which the microwave radiation is ended. This is because ECR continues without the supply of new electrons after the electron avalanche once occurs.

In the above explained second and third embodiments, an electron gun, for example, is applied as the electron supply unit 31. As the electron gun, a thermal electron emission electron gun or a field emission electron gun may be used.

Figure 8:
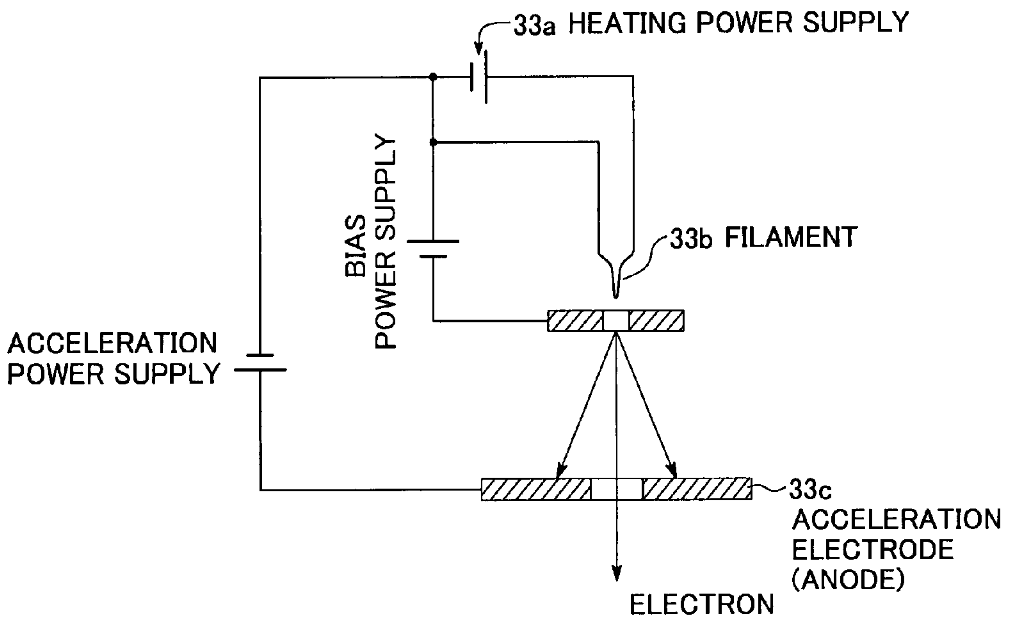
FIG. 8 is a diagram for explanation of an electron generation principle of a thermal electron emission electron gun.

FIG. 8 is a diagram for explanation of an electron generation principle of a thermal electron emission electron gun. As shown in FIG. 8, a filament **33*b* is heated by a heating power supply 33*a*, and thereby, a thermion is generated from the tip of the filament 33*b*. The thermion is accelerated by an acceleration electrode (anode) 33*c*** and emitted.

Figure 9:
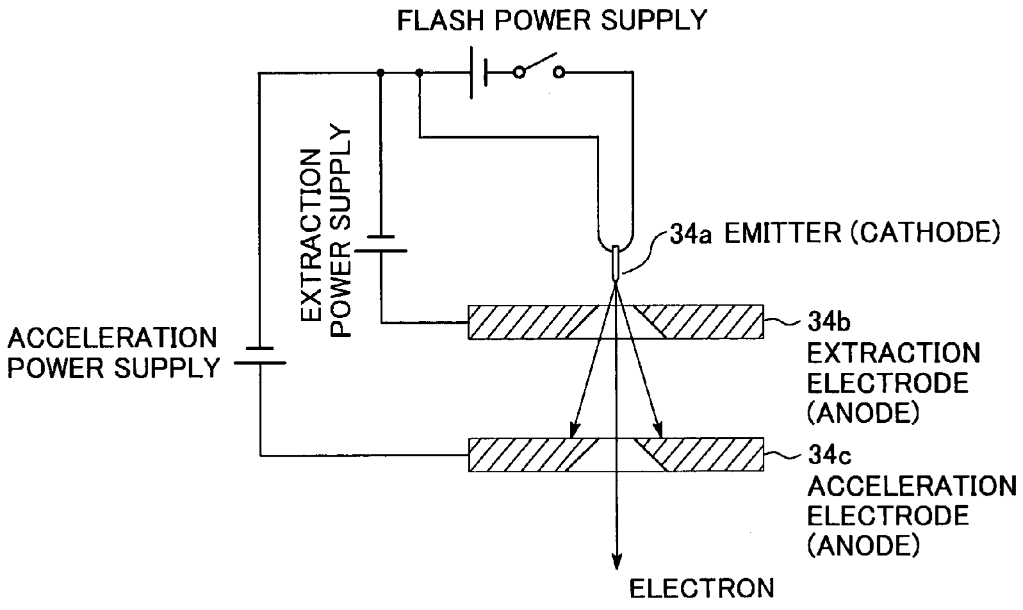
FIG. 9 is a diagram for explanation of an electron generation principle of a field emission electron gun.

Further, FIG. 9 is a diagram for explanation of an electron generation principle of a field emission electron gun. As shown in FIG. 9, a strong electric field is formed by an extraction electrode (anode) **34*a*, and thereby, an electron is generated from the tip of an emitter (cathode) 34*b*. The electron is accelerated by an acceleration electrode (anode) 34*c*** and emitted.

Next, an EUV light source apparatus according to the fourth embodiment of the present invention will be explained with reference to FIG. 10.

Figure 10:
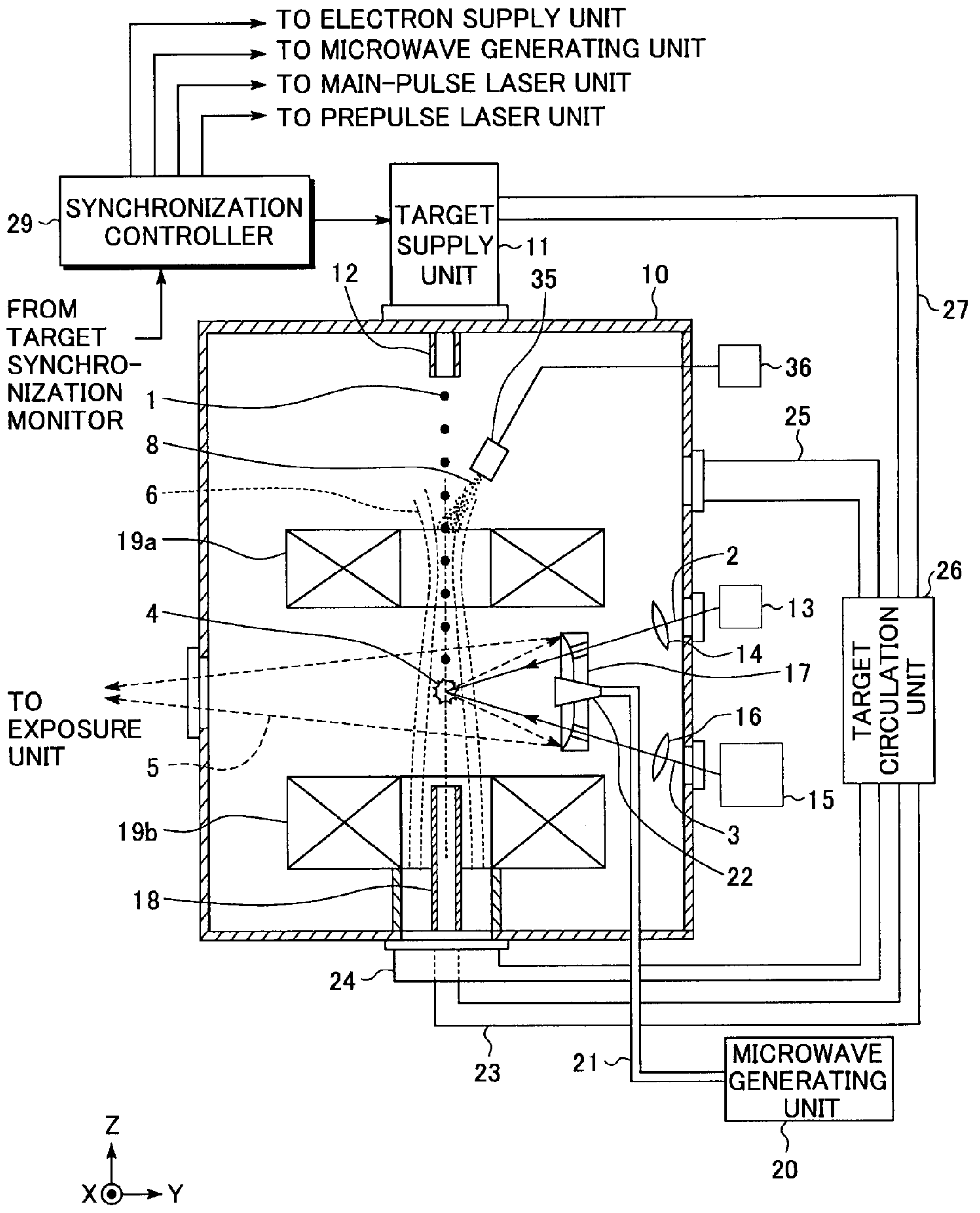
FIG. 10 shows a configuration of an extreme ultra violet light source apparatus according to the fourth embodiment of the present invention.

As shown in FIG. 10, the EUV light source apparatus according to the embodiment has an ultraviolet ionizer 35 and an electron supply controller 36 in place of the electron supply unit 31 and the electron supply controller 32 shown in FIG. 6 and supplies primary electrons 7 according to a principle of ultraviolet ionization. The rest of the configuration is the same as that shown in FIG. 6.

Figure 11:
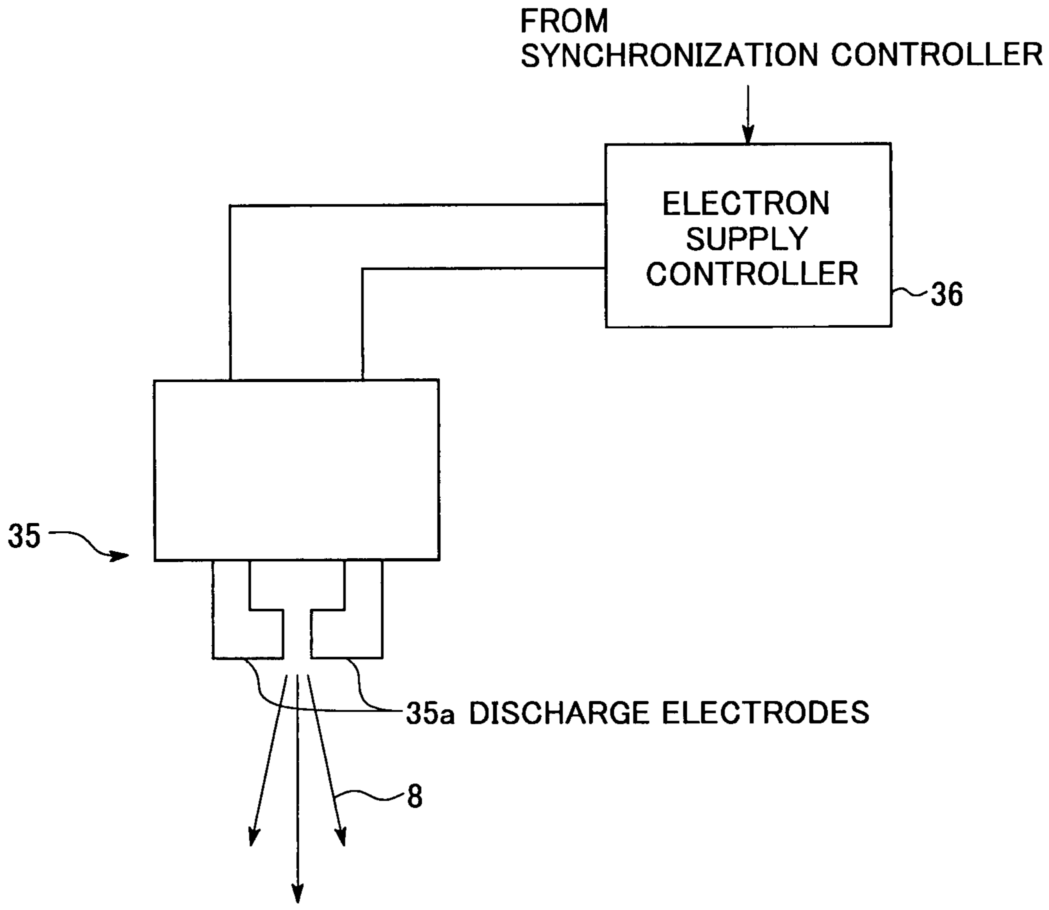
FIG. 11 is a diagram for explanation of an electron supply principle by ultraviolet ionization shown in FIG. 10.

FIG. 11 is a diagram for explanation of an electron supply principle by ultraviolet ionization. The ultraviolet ionizer 35 has a pair of discharge electrodes **35*a* provided facing each other. Further, the electron supply controller 36** includes a high-voltage supply circuit.

When pulse discharge is caused by applying a high voltage to the discharge electrodes **35*a* by the electron supply controller 36, ultraviolet light 8 is generated. When the residual gas around there is irradiated with the ultraviolet light, the residual gas is ionized to generate electrons. Further, when there is residual gas between the discharge electrodes 35*a* as well, the residual gas is ionized by pulse discharge to generate electrons. Thus generated electrons are guided to the vicinity of the plasma emission point along lines of magnetic flux 6 by the effect of the magnetic field formed by electromagnets 19*a* and 19*b* (FIG. 10**), and used as primary electrons in ECR.

The operation of the electron supply controller 36 is controlled by the synchronization controller 29 so as to perform pulse operation based on the radiation start timing of microwave. Desirably, as explained by referring to FIG. 7, the voltage is supplied by the electron supply controller 36 to start discharge earlier than the application timing of prepulse 2 or main pulse 3.

Next, an EUV light source apparatus according to the fifth embodiment of the present invention will be explained with reference to FIG. 12.

Figure 12:
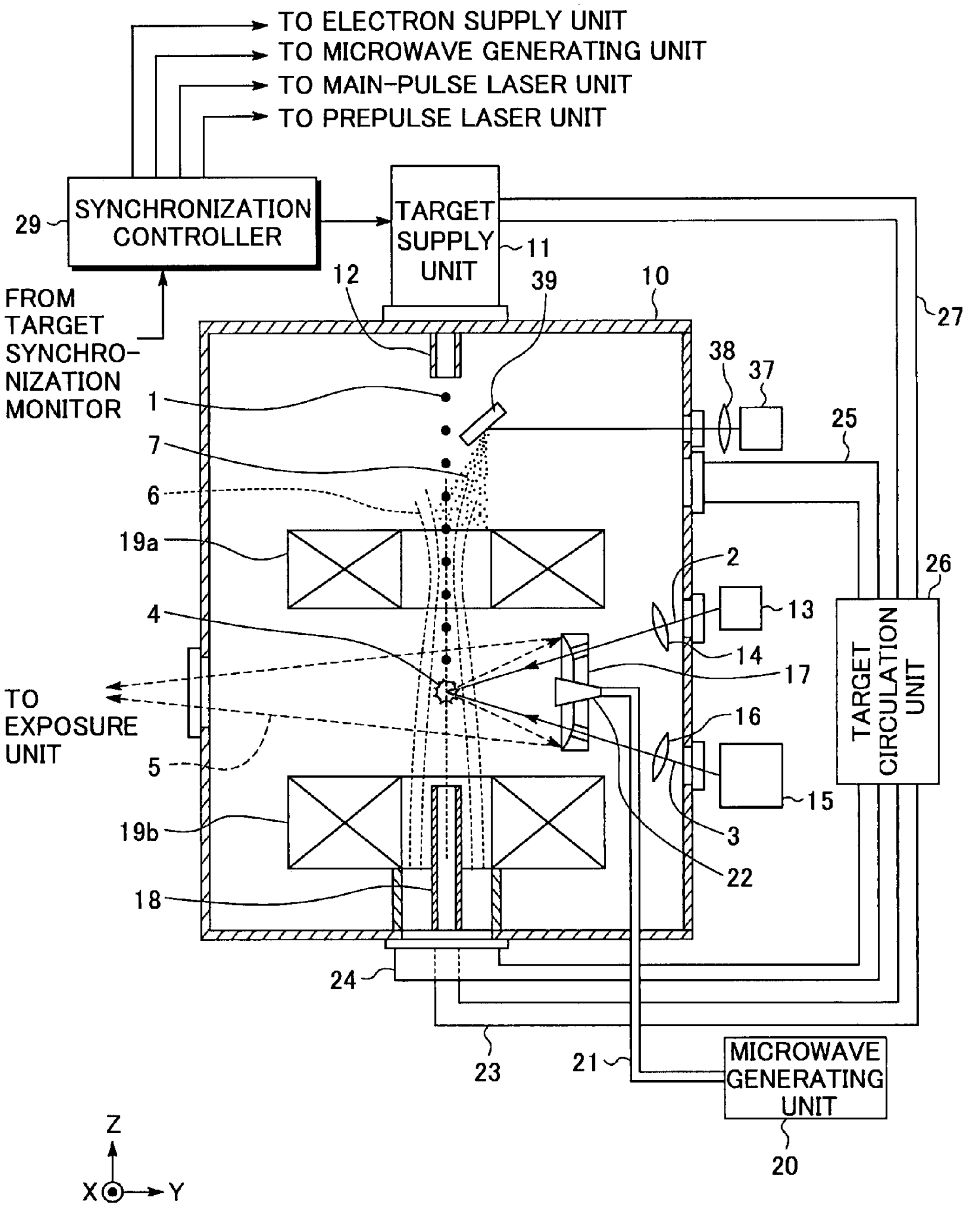
FIG. 12 shows a configuration of an extreme ultra violet light source apparatus according to the fifth embodiment of the present invention.

As shown in FIG. 12, the EUV light source apparatus according to the embodiment has an electron supply laser unit 37, a collective lens 38, and an electron supply target 39 in place of the electron supply unit 31 and the electron supply controller 32 shown in FIG. 6, and supplies primary electrons 7 into the chamber 10 according to a principle of laser-generated plasma. The rest of the configuration is the same as that shown in FIG. 6.

As the electron supply target 39, a material that produces as little debris as possible is desirably used in order to suppress the contamination and damage on the parts in the chamber 10 and the reduction in degree of vacuum within the chamber 10. The target includes a metal spinning target such as tungsten (W) material, an argon (Ar) gas jet target, a helium (He) gas jet target, or the like, for example. The laser beam emitted from the electron supply laser unit 37 is condensed by the collective lens 38 and applied to the electron supply target 39. Thereby, the electron supply target 39 is excited and plasma is generated. The electrons 7 emitted from the plasma are guided to the vicinity of the plasma emission point along lines of magnetic flux 6 by the effect of the magnetic field formed by electromagnets 19*a* and 19*b*, and used as primary electrons in ECR.

Also, in the embodiment, the operation of the electron supply laser unit 37 is controlled by the synchronization controller 29 so as to perform pulse operation based on the radiation start timing of microwave. Desirably, as explained by referring to FIG. 7, the operation of the microwave generating unit 20 and the electron supply laser unit 37 is started earlier than the application timing of prepulse 2 or main pulse 3.

Next, an EUV light source apparatus according to the sixth embodiment of the present invention will be explained with reference to FIG. 13.

Figure 13:
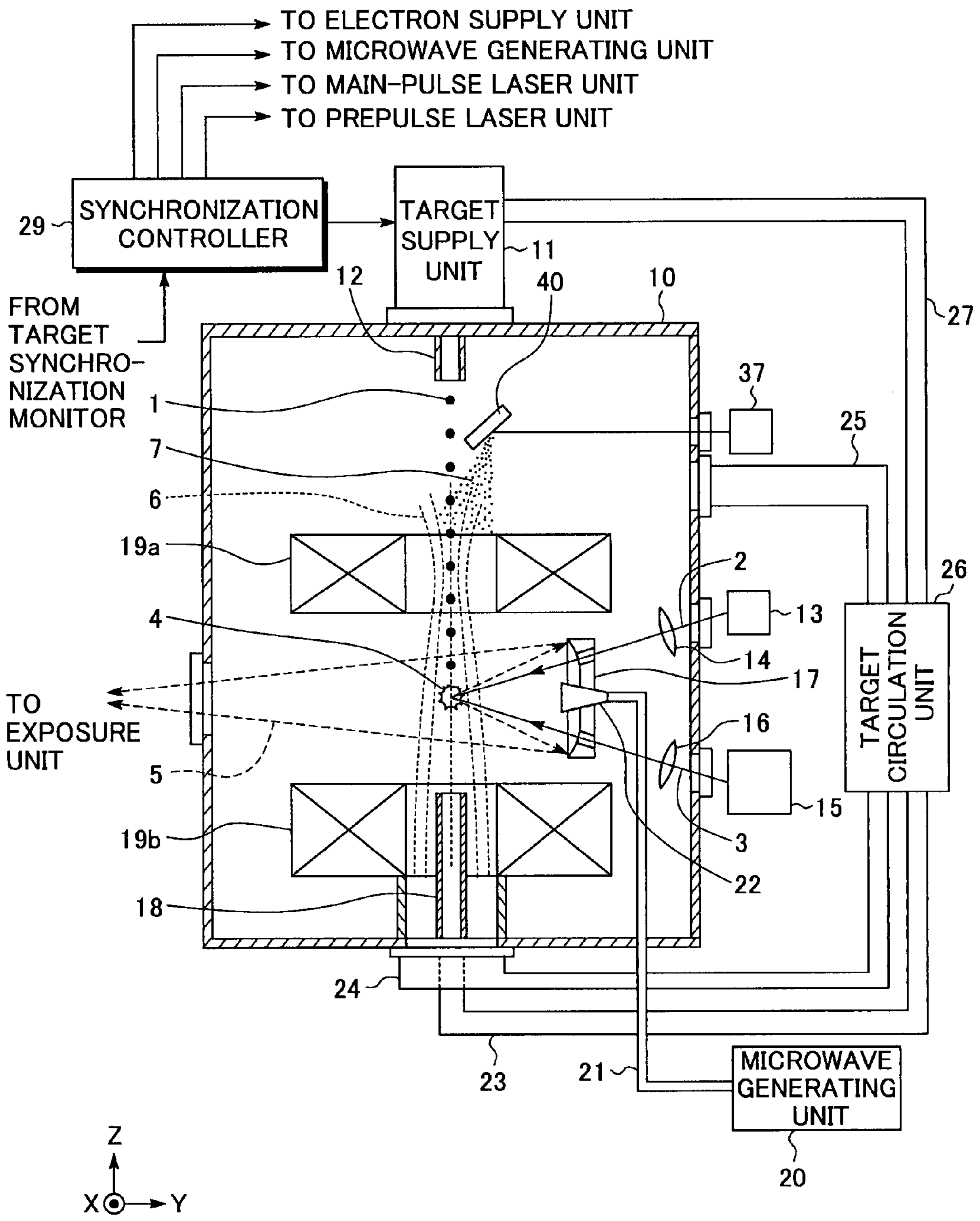
FIG. 13 shows a configuration of an extreme ultra violet light source apparatus according to the sixth embodiment of the present invention.

As shown in FIG. 13, the EUV light source apparatus according to the embodiment has a photoelectron generation target 40 in place of the electron supply target 39, and supplies primary electrons 7 into the chamber 10 according to a principle of photoelectron generation. Further, in the embodiment, the collective lens 38 (FIG. 12) is not provided because it is not necessary to condense the laser beam emitted from the electron supply laser unit 37. The rest of the configuration is the same as that shown in FIG. 12.

As the photoelectron generation target 40, a material that has a small work function of photoelectron generation and produces as little debris as possible is desirably used in order to suppress the contamination and damage on the parts in the chamber 10 and the reduction in degree of vacuum within the chamber 10. The target includes a cesium (Cs) metal plate or an alloy plate target containing cesium, a magnesium (Mg) metal plate or an alloy plate target containing magnesium, a tungsten (W) metal plate target, or the like, for example. The laser beam emitted from the electron supply target 39 is applied to the photoelectron generation target 40, and thereby, the photoelectron generation target 40 is excited and electrons 7 are emitted from the surface thereof. The electrons 7 are guided to the vicinity of the plasma emission point along lines of magnetic flux 6 by the effect of the magnetic field formed by electromagnets 19*a* and 19*b*, and used as primary electrons in ECR.

Also, in the embodiment, the operation of the electron supply laser unit 37 is controlled by the synchronization controller 29 so as to perform pulse operation based on the radiation start timing of microwave. Desirably, as explained by referring to FIG. 7, the operation of the microwave generating unit 20 and the electron supply laser unit 37 is started earlier than the application timing of prepulse 2 or main pulse 3.

Next, an EUV light source apparatus according to the seventh embodiment of the present invention will be explained with reference to FIG. 14.

Figure 14:
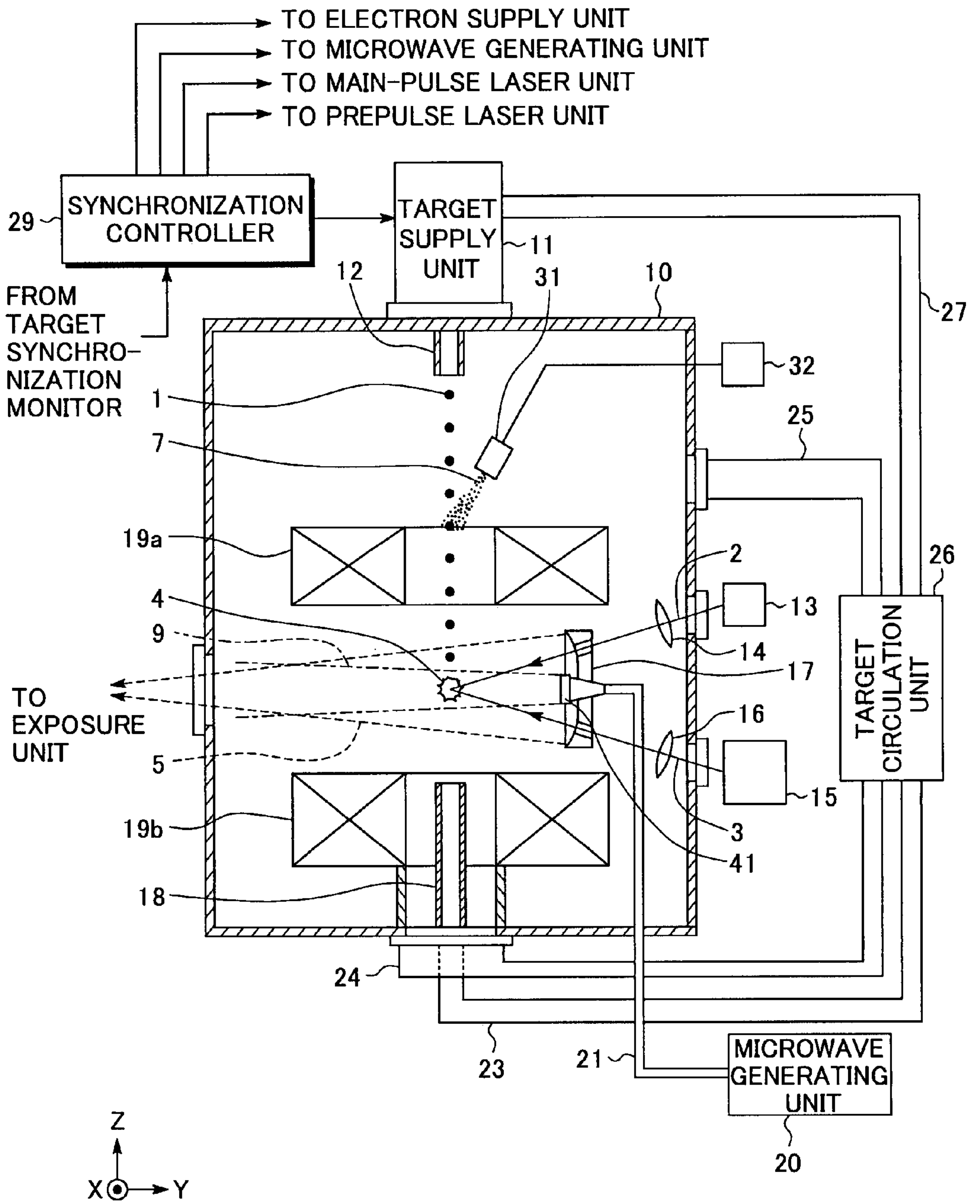
FIG. 14 shows a configuration of an extreme ultra violet light source apparatus according to the seventh embodiment of the present invention.

As shown in FIG. 14, the EUV light source apparatus according to the embodiment is provided with a microwave highly directing unit 41 in place of or in addition to the microwave antenna 22 shown in FIG. 6. The rest of the configuration is the same as that shown in FIG. 6.

Figure 15:
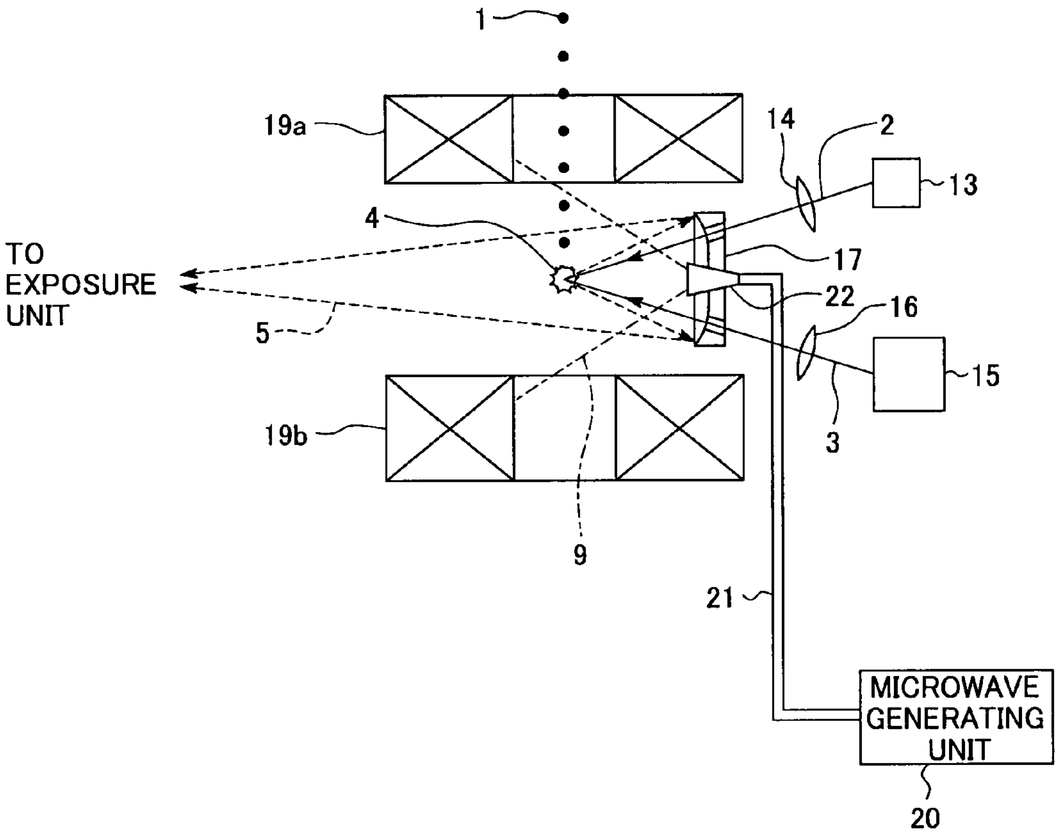
FIG. 15 shows a radiation range of microwave radiated from a microwave antenna.

Here, by referring to FIG. 15, typically, microwave 9 radiated from an aperture antenna in a horn shape (horn antenna) diverges within the chamber 10. On the other hand, a region where the microwave 9 should be applied for ionizing neutral particles by ECR is limited to a range of about 1 cm to several centimeters in which the plasma 4 expands in several nanoseconds to several tens of nanoseconds assuming that the expansion speed of the plasma 4 is about several kilometers per second. Accordingly, the ratio of the microwave energy actually used for ionization by ECR to the entire microwave energy radiated into the chamber 10 is very small. That is, the microwave intensity is insufficient in the region requiring microwave application, and unwanted microwave energy is supplied into the chamber 10.

In the embodiment, since the microwave highly directing unit 41 is provided, the microwave 9 can be concentrated onto the region of about 1 cm to several centimeters around the plasma emission point. Thereby, the effective use of microwave energy can be realized and the loss of stability in droplet target generation due to unwanted microwave energy can be suppressed.

Next, a specific configuration of the microwave highly directing unit 41 shown in FIG. 14 will be explained with reference to FIGS. 16-18.

Figure 16:
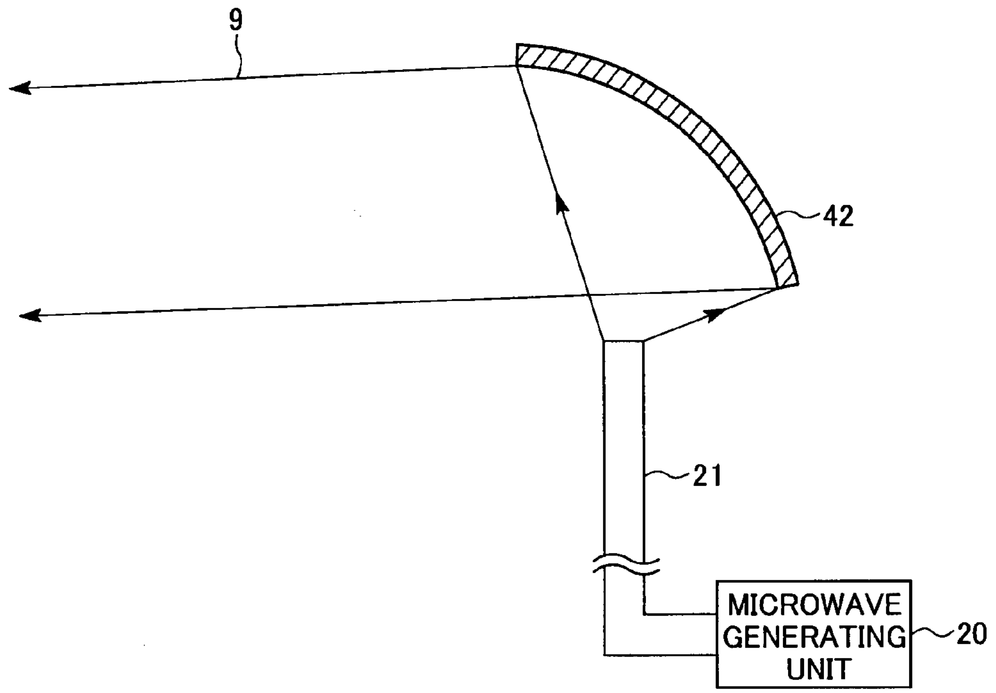
FIG. 16 shows an example of forming a microwave highly directing unit by employing a microwave parabolic mirror.

FIG. 16 shows an example of forming a microwave highly directing unit with a microwave parabolic mirror 42. In this case, the microwave that has propagated through the microwave waveguide 21 is entered into the microwave parabolic mirror 42. Here, the incident wave incident to the parabolic surface is reflected in a predetermined direction regardless of the incident angle, and thereby, the microwaves 9 propagating in parallel can be formed.

Figure 17:
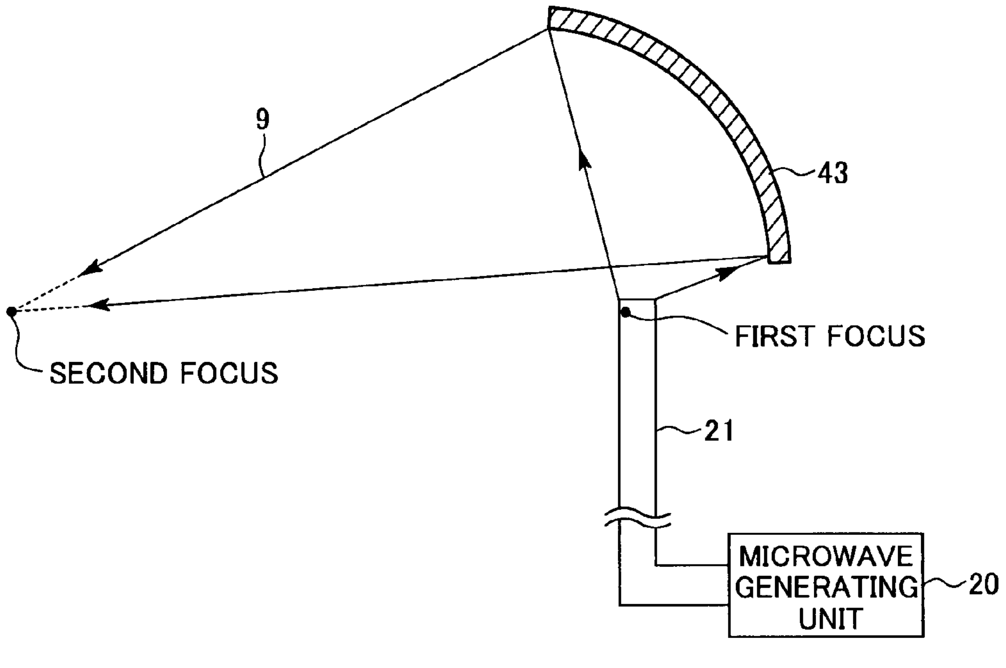
FIG. 17 shows an example of forming a microwave highly directing unit by employing a microwave spheroidal mirror.

FIG. 17 shows an example of forming a microwave highly directing unit with a microwave spheroidal mirror 43. In this case, the microwave spheroidal mirror 43 is provided such that the first focus is located near the end of the microwave waveguide 21 and the second focus is located near the plasma emission point, and the microwave is entered into the reflecting surface thereof. Here, the incident wave that has passed through the first focus of the spheroidal mirror and entered the spheroidal surface is reflected in a direction toward the second focus of the spheroidal surface, and thereby, the microwaves 9 can be focused near the plasma emission point.

Figure 18:
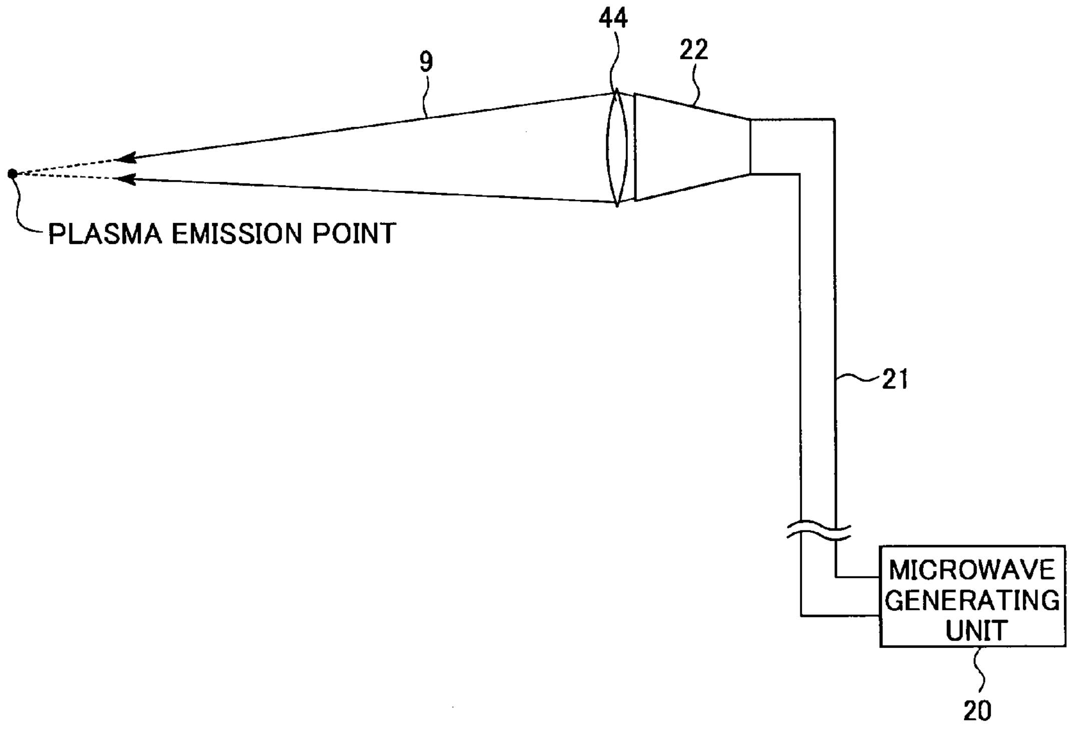
FIG. 18 shows an example of forming a microwave highly directing unit by employing a dielectric microwave lens.

FIG. 18 shows an example of forming a microwave highly directing unit by providing a dielectric microwave lens (collective lens) 44 on the tip of the microwave antenna 22. Here, the dielectric microwave lens 44 is a microwave lens formed of a dielectric material such as ceramics and Teflon (registered trademark), and acts on the microwave in the same manner as that an optical lens acts on light. In this case, the dielectric microwave lens 44 is provided such that its focus is located near the plasma emission point. Thereby, the microwaves 9 radiated from the microwave antenna 22 can be focused near the plasma emission point.

As described above, according to the embodiment, since the directivity of microwave is made higher, the microwave having sufficient intensity can be concentrated in the range in which the plasma expands within a predetermined period.

In the above explained first to seventh embodiments, the LPP system has been used as the plasma generation system in the EUV light source apparatus, however, a discharge produced plasma (DPP) system may be used instead. Here, the DPP system is a system for generating plasma by providing discharge energy to a plasma generation material (discharge emission gas).

Figure 19:
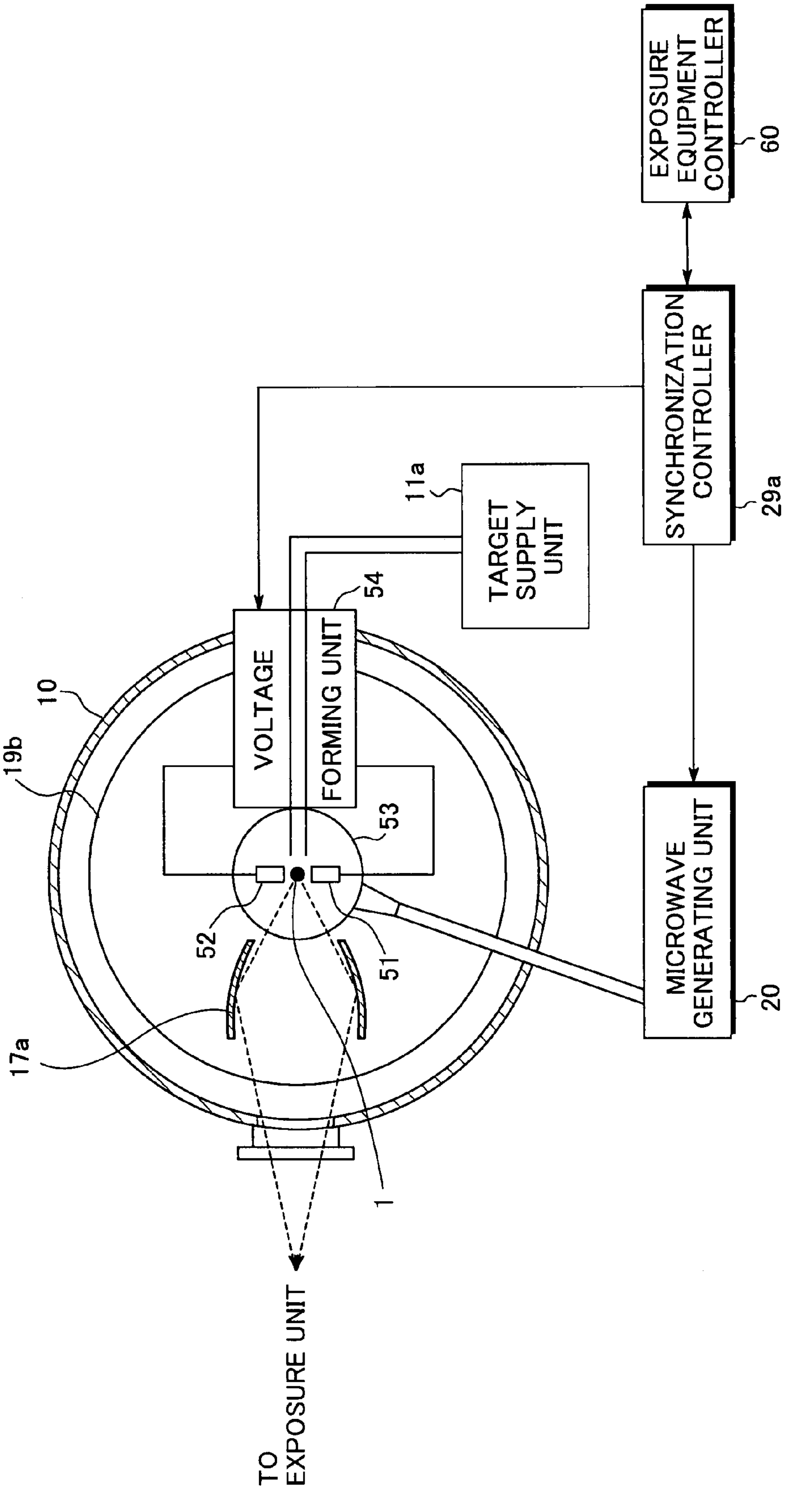
FIG. 19 shows a section of an extreme ultra violet light source apparatus according to DPP system.

FIG. 19 shows a section of an extreme ultra violet light source apparatus according to DPP system. In the DPP system, a discharge part 53, in which opposed electrodes 51 and 52 are formed, is provided, a target supply unit 11*a* supplies a target material 1 to the discharge part 53, and a voltage forming unit 54 forms a voltage through pulse operation and supplies the voltage between the electrodes 51 and 52.

As the target material 1 to become a plasma source, xenon (Xe), tin (Sn), or compound including tin (Sn) can be used. The target supply unit 11*a* supplies the target material 1 in a form of gas, liquid droplet, or the like to a space between the electrodes 51 and 52 or to the vicinity of the electrodes 51 and 52. In the case where the target material is supplied in a form of liquid droplet, the target material may be irradiated with a laser beam by a laser apparatus (not shown in the drawing) to generate a gaseous material due to ablation, and the gaseous material may be supplied to the electrodes 51 and 52. Alternately, a target material in a liquid state may be applied to the electrodes 51 and 52, and the target material may be turned into a gaseous state due to ablation and supplied to the electrodes 51 and 52.

Further, in the DPP system, an EUV collector mirror 17*a* of a slant incident type such as a mirror having a form of spheroid or a mirror of a Wolter type is employed. Usually, on a reflecting surface of the EUV collector mirror 17*a* of a slant incident type, a single layer of metal reflecting film is formed. Alternatively, an EUV collector mirror, in which plural reflecting surfaces are combined telescopically, may be employed.

In the DPP EUV light source apparatus, by additionally providing magnetic field forming means (the electromagnets 19*a* and 19*b*), microwave radiating means (the microwave generating unit 20 to microwave antenna 22 and the microwave highly directing unit 41), synchronization control means (the synchronization controller 29*a*), electron supply means (the electron supply unit 31 to the photoelectron generation target 40), and so on, neutral debris generated from the plasma can be efficiently ionized by ECR and can be immediately exhausted to the outside of the EUV collector mirror by the effect of the magnetic field. The synchronization controller 29*a* as shown in FIG. 19 is connected to an exposure equipment controller, and controls the microwave generating unit 20, the voltage forming unit 54, and so on.

The invention claimed is:

1. An extreme ultra violet light source apparatus comprising:

- a plasma generating unit that generates plasma through pulse operation of a laser beam to target material so as to radiate extreme ultra violet light;
- collective optics that collects the extreme ultra violet light radiated from the plasma;
- a microwave radiating unit that radiates microwaves through pulse operation into a space in which a magnetic field is formed to cause electron cyclotron resonance so as to ionize neutral particles emitted from the plasma;
- a magnetic field forming unit that forms said magnetic field and a magnetic field for trapping at least ionized particles; and
- a control unit that synchronously controls at least said plasma generating unit and said microwave radiating unit.

2. The extreme ultra violet light source apparatus according to claim 1, wherein said plasma generating unit includes:

- a target supply unit that supplies a target material;
- a target nozzle that injects the target material supplied by said target supply unit; and
- a laser unit that applies a laser beam through pulse operation to the target material injected from said target nozzle so as to generate the plasma.

3. The extreme ultra violet light source apparatus according to claim 2, wherein said plasma generating unit further includes:

- a second laser unit that applies a laser beam through pulse operation to the target material injected from said target nozzle so as to change density of the target material.

4. The extreme ultra violet light source apparatus according to claim 1, wherein said plasma generating unit further includes:

- a discharge unit having opposed electrodes;
- a plasma generating material supply unit that supplies a plasma generating material that discharges between the electrodes when a voltage is supplied between the electrodes; and
- a voltage forming unit that forms the voltage to be supplied between the electrodes through pulse operation so as to generate the plasma.

5. The extreme ultra violet light source apparatus according to claim 1, wherein said control unit synchronously controls said plasma generating unit and said microwave radiating unit such that said microwave radiating unit starts operation earlier than said plasma generating unit.

6. The extreme ultra violet light source apparatus according to claim 1, further comprising:

- a electron supply unit for supplying electrons into a region where microwave is applied by said microwave radiating unit.

7. The extreme ultra violet light source apparatus according to claim 6, wherein said control unit synchronously controls said plasma generating unit, said microwave radiating unit, and said electron supply unit.

8. The extreme ultra violet light source apparatus according to claim 7, wherein said control unit synchronously controls said plasma generating unit, said microwave radiating unit, and said electron supply unit such that said microwave radiating unit and said electron supply unit start operation earlier than said plasma generating unit.

9. The extreme ultra violet light source apparatus according to claim 6, wherein said electron supply unit includes an electron gun.

10. The extreme ultra violet light source apparatus according to claim 6, wherein said electron supply unit includes a discharge electrode and means for supplying a voltage to the discharge electrode.

11. The extreme ultra violet light source apparatus according to claim 6, wherein said electron supply unit includes:

- a target material that generates plasma when a laser beam is applied thereto; and
- a laser unit that emits a laser beam to be applied to the target material.

12. The extreme ultra violet light source apparatus according to claim 6, wherein said electron supply unit includes:

- a target material that emits photoelectrons when a laser beam is applied thereto; and
- a laser unit that emits a laser beam to be applied to the target material.

13. The extreme ultra violet light source apparatus according to claim 1, further comprising:

- a microwave highly directing unit for making directivity of microwave applied from said microwave radiating unit higher.

14. The extreme ultra violet light source apparatus according to claim 13, wherein said microwave highly directing unit includes at least one of a microwave parabolic mirror, a microwave spheroidal mirror, and a dielectric microwave lens.

15. The extreme ultraviolet light source apparatus according to claim 1, wherein said control unit synchronously controls said plasma generating unit and said microwave radiating unit such that said microwave radiating unit is radiated in pulse in synchronization with plasma generation.

16. An extreme ultra violet light source apparatus comprising:

plasma generating means for generating plasma through pulse operation of a laser beam to target material so as to radiate extreme ultra violet light;

collective optics that collects the extreme ultra violet light radiated from the plasma;

microwave radiating means for radiating microwaves through pulse operation into a space in which a magnetic field is formed to cause electron cyclotron resonance so as to ionize neutral particles emitted from the plasma;

magnetic field forming means for forming said magnetic field and a magnetic field for trapping at least ionized particles; and control means for synchronously controlling at least said plasma generating means and said microwave radiating means.

17. The extreme ultra violet light source apparatus according to claim 16, wherein said control means synchronously controls said plasma generating means and said microwave radiating means such that said microwave radiating means starts operation earlier than said plasma generating means.

18. The extreme ultra violet light source apparatus according to claim 16, further comprising:

electron supply means for supplying electrons into a region where microwave is applied by said microwave radiating means.

19. The extreme ultra violet light source apparatus according to claim 18, wherein said control means synchronously controls said plasma generating means, said microwave radiating means, and said electron supply means such that said microwave radiating means and said electron supply means start operation earlier than said plasma generating means.

20. The extreme ultraviolet light source apparatus according to claim 16, wherein said control means synchronously controls said plasma generating means and said microwave radiating means such that said microwave radiating means is radiated in pulse in synchronization with plasma generation.

* * * * *